(12) United States Patent
Arwidsson et al.

(10) Patent No.: US 11,065,325 B2
(45) Date of Patent: Jul. 20, 2021

(54) VACCINE COMPOSITION FOR NAIVE SUBJECTS

(71) Applicant: Eurocine Vaccines AB, Solna (SE)

(72) Inventors: Hans Arwidsson, Strängnäs (SE); Anna-Karin Maltais, Spånga (SE)

(73) Assignee: Eurocine Vaccines AB, Soina (SE)

( * ) Notice: Subject to any disclaimer, the term of this patent is extended or adjusted under 35 U.S.C. 154(b) by 0 days.

(21) Appl. No.: 14/650,809

(22) PCT Filed: Dec. 17, 2013

(86) PCT No.: PCT/EP2013/077006
§ 371 (c)(1),
(2) Date: Jun. 9, 2015

(87) PCT Pub. No.: WO2014/095943
PCT Pub. Date: Jun. 26, 2014

(65) Prior Publication Data
US 2015/0306205 A1 Oct. 29, 2015

(30) Foreign Application Priority Data

Dec. 17, 2012 (EP) ..................... 12197522

(51) Int. Cl.
*A61K 39/12* (2006.01)
*A61K 45/00* (2006.01)
(Continued)

(52) U.S. Cl.
CPC ............ *A61K 39/145* (2013.01); *A61K 39/12* (2013.01); *A61K 39/39* (2013.01); *C12N 7/00* (2013.01);
(Continued)

(58) Field of Classification Search
None
See application file for complete search history.

(56) References Cited

U.S. PATENT DOCUMENTS 6,890,540 B1  5/2005  Schroder et al.
7,128,909 B2  10/2006  Schroder et al.
(Continued)

FOREIGN PATENT DOCUMENTS

JP  2000-512292 A  9/2000
RU  2390351 C2  9/2007
(Continued)

OTHER PUBLICATIONS

Fleming et al., "Health Benefits, Risks, and Cost-Effectiveness of Influenza Vaccination in Children," The Pediatric Infectious Disease Journal, vol. 27, No. 11, S154-S158 (2008).*
(Continued)

*Primary Examiner* — M Franco G Salvoza
(74) *Attorney, Agent, or Firm* — Knobbe, Martens, Olson & Bear LLP

(57) ABSTRACT

The invention relates to nasally-administered vaccine compositions effective in naive subjects such as children. Further, the vaccine composition is suitable for vaccinating the general population during a pandemic. One aspect of the invention is directed to the paediatric use of the vaccine of the invention including a vaccine effective in children against seasonal influenza virus strains. A further aspect of the invention is directed to subjects of all age groups when the composition is for pandemic use.

11 Claims, 8 Drawing Sheets

(51) Int. Cl.
  *A61K 39/145* (2006.01)
  *A61K 39/39* (2006.01)
  *C12N 7/00* (2006.01)
  *A61K 39/00* (2006.01)
(52) U.S. Cl.
  CPC .............. *A61K 2039/5252* (2013.01); *A61K 2039/543* (2013.01); *A61K 2039/55511* (2013.01); *A61K 2039/55588* (2013.01); *A61K 2039/58* (2013.01); *C12N 2760/16134* (2013.01); *Y02A 50/30* (2018.01)

(56) References Cited

U.S. PATENT DOCUMENTS

| | | |
|---|---|---|
| 8,211,442 B2 | 7/2012 | Kido et al. |
| 8,410,248 B2 | 4/2013 | Rosen et al. |
| 2005/0208602 A1 | 9/2005 | Rosen et al. |
| 2006/0073561 A1 | 4/2006 | Rosen et al. |
| 2009/0130131 A1 | 5/2009 | Kido et al. |
| 2009/0291095 A1 | 11/2009 | Baker et al. |
| 2010/0197951 A1 | 8/2010 | Fang et al. |
| 2010/0260797 A1 | 10/2010 | Hanon |
| 2012/0088817 A1 | 4/2012 | Collard et al. |
| 2012/0107349 A1 | 5/2012 | Baker et al. |
| 2013/0178383 A1 | 7/2013 | Spetzler et al. |

FOREIGN PATENT DOCUMENTS

| | | |
|---|---|---|
| WO | WO 97/47320 A1 | 12/1997 |
| WO | WO 02/080648 A2 | 10/2002 |
| WO | WO 2004/047862 A1 | 6/2004 |
| WO | WO 2006/125076 A2 | 11/2006 |
| WO | WO 2012/042003 A1 | 4/2012 |
| WO | WO 2012042003 A1 | 4/2012 |

OTHER PUBLICATIONS

Harper et al., "Seasonal Influenza in Adults and Children-Diagnosis, Treatment, Chemoprophylaxis, and Institutional Outbreak Management: Clinical Practice Guidelines of the Infectious Diseases Society of America," Clinical Infectious Diseases 48:1003-32 (2009).*
Organic Materials Review Institute, "National Organic Standards Board Technical Advisory Panel Review: Glycerol Monooleate", compiled for the USDA National Organic Program, pp. 1-16 (2001).*
Tosh et al., "Influenza Vaccines: From Surveillance Through Production to Protection," Mayo Clin Proc. 85(3):257-273 (2010).*
World Health Organization, "Information Sheet: Observed Rate of Vaccine Reactions: Influenza Vaccine," Global Vaccine Safety, Immunization, Vaccines and Biologicals (Year: 2012).*
Rowhani-Rahbar et al., "Immunization and Bell's Palsy in Children: A Case-Centered Analysis," American Journal of Epidemiology, vol. 175, No. 9: 878-885 (Year: 2012).*
Buonaguro, L. et al., "DNA-VLP prime-boost intra-nasal immunization induces cellular and humoral anti-HIV-1 systemic and mucosal immunity with cross-clade neutralizing activity" Vaccine, 2007, pp. 5968-5977, vol. 25.
Esposito, Susanna et al., "Vaccinations in children with cancer" Vaccine, 2010, pp. 3278-3284, vol. 28.
Esposito, Susanna et al., "Different influenza vaccine formulations and adjuvants for childhood influenza vaccination" Vaccine, 2011, pp. 7535-7541, vol. 29.
Falkeborn, Tina et al., "Endocine™, N3OA and N3OASq; Three Mucosal Adjuvants That Enhance the Immune Response to Nasal Influenza Vaccination" PLOS One, Aug. 2013, pp. 1-9, vol. 8, Issue 8, e70527, XP009172690.
Glück, T. "Vaccinate your immunocompromised patients!" Rheumatology, 2006, pp. 9-10, vol. 45.
Haile, M. et al., "Immunization with heat-killed *Mycobacterium bovis* bacille Calmette-Guerin (BCG) in Eurocine™ L3 adjuvant protects against tuberculosis" Vaccine, 2004, pp. 1498-1508, vol. 22.

Hakim, Hana et al., "Immunogenicity and safety of inactivated monovalent 2009 H1N1 influenza A vaccine in immunocompromised children and young adults" Vaccine, 2012, pp. 879-885, vol. 30.
Hinkula, Jorma et al., "A novel DNA adjuvant, N3, enhances mucosal and systemic immune responses induced by HIV-1 DNA and peptide immunizations" Vaccine, 2006, pp. 4494-4497, vol. 24.
Petersson, Pernilla et al., "The Eurocine® L3 adjuvants with subunit influenza antigens induce protective immunity in mice after intranasal vaccination" Vaccine, 2010, pp. 6491-6497, vol. 28.
Schröder, Ulf et al., "Nasal and parenteral immunizations with diphtheria toxoid using monoglyceride/fatty acid lipid suspensions as adjuvants" Vaccine, 1999, pp. 2096-2103, vol. 17.
International Search Report for PCT/EP2013/077006 dated Mar. 3, 2014.
Ofuji Satoko, et al., Targets for vaccination against influenza, Japan Public Health Magazine, Jun. 15, 2007, vol. 54, No. 6, p. 361-367.
Japanese Office Action dated Aug. 2, 2017, in corresponding Japanese Patent Application No. 2015-547077.
Ambrose et al. "The safety and effectiveness of self-administration of intranasal live attenuated influenza vaccine in adults" Vaccine, 2013, pp. 857-860, vol. 31.
Barchfeld et al. Vaccine, 1999, 17, 695-704.
Couch, Robert B. "Nasal Vaccination, *Escherichia coli* Enterotoxin, and Bell's Palsy" The New England Journal of Medicine, Feb. 26, 2004, pp. 860-861, vol. 350, No. 9.
Hamasur, Beston et al., "*Mycobacterium tuberculosis* arabinomannan-protein conjugates protect against tuberculosis" Vaccine, 2003, pp. 4081-4093, vol. 21.
Hinkula, Jorma et al., "Safety and immunogenicity, after nasal application of HIV-1 DNA gagp37 plasmid vaccine in young mice" Vaccine, 2008, pp. 5101-5106, vol. 26.
Joseph, Aviva et al., "A new intranasal influenza vaccine based on a novel polycationic lipid-ceramide carbamoyl-spermine (CCS) I. Immunogenicty and efficacy studies in mice" Vaccine, 2006, pp. 3990-4006, vol. 24.
Kendall, Mark "Vaccinating against influenza in children without needles: A new initiative" Journal of Pediatric Infectious Diseases, 2012, pp. 83-88, vol. 7.
Lewis, David J.M. et al., "Transient Facial Nerve Paralysis (Bell's Palsy) following Intranasal Delivery of a Genetically Detoxified Mutant of *Escherichia coli* Heat Labile Toxin" PLoS One, Sep. 2009, pp. 1-5, vol. 4, Issue 9.
Mutsch, Margot et al., "Use of the Inactivated Intranasal Influenza Vaccine and the Risk of Bell's Palsy in Switzerland" The New England Journal of Medicine, Feb. 26, 2004, pp. 896-903, vol. 350, No. 9.
Nichol, Kristin et al., "Effectiveness of Live, Attenuated Intranasal Influenza Virus Vaccine in Healthy, Working Adults" JAMA, Jul. 14, 1999, pp. 137-144, vol. 281, No. 2.
Nichol, Kristin L. "Live attenuated influenza virus vaccines: new options for the prevention of influenza" Vaccine, 2001, pp. 4373-4377, vol. 19.
Rosenberg, Steven et al., "Different Adjuvanticity of Incomplete Freund's Adjuvant Derived From Beef or Vegetable Components in Melanoma Patients Immunized With a Peptide Vaccine" J Immunother, Jul.-Aug. 2010, pp. 626-629, vol. 33, No. 6.
Sekiya, M., Juntendo Medical Journal 55(3):240-244 (2009).
Slingluff, Craig L. et al., "Immunogenicity for CD8+ and CD4+ T Cells of 2 Formulations of an Incomplete Freund's Adjuvant for Multipeptide Melanoma Vaccines" J Immunother, Jul.-Aug. 2010, pp. 630-638, vol. 33, No. 6.
Takeshi Tanimoto. Apr. 28, 2010. Development of intranasal influenze vaccine. *Drug Delivery System*, vol. 25, No. 1, pp. 15-21.
Weinstock et al., "Prolonged shedding of multidrug-resistant influenza A virus in an immunocompromised patient" N Engl J Med, 348, 867-868, 2003.
Zhou et al., Pharmacoepidemiology and Drug Safety, 2004; 13: 505-510.
ClinicalTrials.gov archive—View of NCT00085189—Dated: Feb. 8, 2009 Title: A Phase II Trial of a Vaccine Combining Multiple Class I Peptides With Montanide ISA 51 and ISA 51 VG and CpG Adjuvant 7909 for Patients With Resected Stages IIC/III and IV Melanoma.

(56) References Cited

OTHER PUBLICATIONS

ClinicalTrials.gov archive—View of NCT00935545—Dated: Jul. 8, 2009 Title: A Phase I Study of Peptide Vaccination With Tumor Associated Antigens Mixed With Montanide ISA51VG in Pediatric Patients With Recurrent or Refractory Central Nervous System Tumors.

ClinicalTrials.gov archive—View of NCT01079741—Dated: Sep. 16, 2010 Title: Phase I/Phase II Open Label Study of the TLR3 Agonist PolyICLC as an Adjuvant for NYESO1 Protein Vaccination With or Without Montanide® ISA51 VG in Patients With High Risk Melanoma in Complete Clinical Remission.

ClinicalTrials.gov archive—View of NCT01176461—Dated: Aug. 5, 2010 Title: A Pilot Trial of a Vaccine Combining Multiple Class I Peptides and Montanide ISA 51 VG With Escalating Doses of AntiPD1 Antibody BMS936558 for Patients With Unresectable Stages III/IV Melanoma.

"Positive Results from Eurocine Vaccines Clinical Phase I/II Study with the Nasal Influenza Vaccine" Eurocine, Press release, Jul. 9, 2010.

Baras B, et al., Longevity of the protective immune response induced after vaccination with one or two doses of AS03A-adjuvanted split H5N1 vaccine in ferrets, Vaccine, Jan. 13, 2011, vol. 29, No. 11, p. 2092-2099.

Baras B, et al., Pandemic H1N1 vaccine requires the use of an adjuvant to protect against challenge in naive ferrets, Vaccine, Jan. 14, 2011, vol. 29, No. 11, p. 2120-2126.

Lambkin R, et al., Strong local and systemic protective immunity induced in the ferret model by an intranasal virosome-formulated influenza subunit vaccine, Vaccine, 2004, vol. 22, No. 31-32, p. 4390-4396.

Office Action dated May 2, 2018 for CA 2810597, filed Sep. 30, 2011.

Office Action dated Apr. 19, 2018 for JP 2015-547078, filed Apr. 30, 2011.

\* cited by examiner

Table 3

|  |  | Group[a] | | | | |
|---|---|---|---|---|---|---|
|  |  | 1 | 2 | 3 | 4 | 5 |
| Clinical score | Survival | 6/6 | 5/6 | 5/6 | 6/6 | 5/6 |
|  | Fever | 1.7±0.5 (6/6) | 1.1±0.4 (6/6) | 1.3±0.3(6/6) | 1.2±0.6(4/5*) | 1.1±0.6(6/6) | 1.3±0.2(6/6) |
|  | Body weight loss | 18.0±4.6 (6/6) | 11.5±2.1 (6/6) | -2.2±2.6 (1/6) | 1.7±1.5 (4/6) | 2.7±3.3 (4/6) | 4.7±3.1 (6/6) |
| Virology | Lung virus load [$\log_{10}TCID_{50}/g$] | 5.7±0.5 (6/6) | 5.5±0.9 (6/6) | ≤1.5 (0/6) | ≤1.4 (0/6) | ≤1.3 (0/6) | ≤1.3 (0/6) |
|  | Turbinates virus load [$\log_{10}TCID_{50}/g$] | 7.2±2.4 (6/6) | 6.9±1.5 (6/6) | ≤1.9 (0/6) | ≤1.7 (0/6) | ≤1.7 (0/6) | 4.1±2.7 (3/6) |
|  | Virus shedding in nasal swabs | 2.5 (5/6) | 1.2 (4/6) | 0.058 (1/6) | 0.0 (0/6) | 0.0 (0/6) | 1.4 (3/6) |
|  | Virus shedding in throat swabs | 10 (6/6) | 10 (6/6) | 0.0 (1/6) | 0.14 (1/6) | 0.0 (1/6) | 4.2 (5/6) |
| Gross pathology | Affected lung tissue [%] | 50±25 (6/6) | 37±21 (6/6) | 8±4 (5/6) | 7±5 (4/6) | 7±5 (4/6) | 8±4 (5/6) |
|  | Relative lung weight | 1.5±0.5 | 1.3±0.1 | 0.8±0.1 | 0.8±0.1 | 0.8±0.2 | 0.9±0.1 |

FIG. 5

Table 4

| Histopathology | | Group[a] | | | | | |
|---|---|---|---|---|---|---|---|
| | | 1 | 2 | 3 | 4 | 5 | 6 |
| | Extent of alveolitis/alveolar damage (score 0-3) | 2.08±0.74 (6/6) | 1.88±0.54 (6/6) | 0.42±0.52 (3/6) | 0.08±0.20 (1/6) | 0.04±0.10 (1/6) | 0.42±0.41 (4/6) |
| | Severity of alveolitis (score 0-3) | 2.04±0.68 (6/6) | 1.63±0.31 (6/6) | 0.50±0.69 (3/6) | 0.08±0.20 (1/6) | 0.04±0.10 (1/6) | 0.46±0.46 (4/6) |
| | Alveolar oedema (% slides positive) | 29±29 (4/6) | 21±19 (4/6) | 4±10 (1/6) | 0±0 (0/6) | 0±0 (0/6) | 8±13 (2/6) |
| | Alveolar haemorrhage (% slides positive) | 21±40 (2/6) | 17±26 (2/6) | 0±0 (0/6) | 0±0 (0/6) | 0±0 (0/6) | 0±0 (0/6) |
| | Type II pneumocyte hyperplasia (% slide positive) | 42±34 (4/6) | 46±37 (4/6) | 8±20 (1/6) | 4±10 (1/6) | 0±0 (0/6) | 4±10 (1/6) |

FIG. 6

VACCINE COMPOSITION FOR NAIVE SUBJECTS

CROSS REFERENCE TO RELATED APPLICATIONS

This application is a U.S. National Phase Application of PCT International Application Number PCT/EP2013/077006, filed on Dec. 17, 2013, designating the United States of America and published in the English language, which is an International Application of and claims the benefit of priority to European Patent Application No. 12197522.1, filed on Dec. 17, 2012. The disclosures of the above-referenced applications are hereby expressly incorporated by reference in their entireties.

FIELD OF INVENTION

The invention relates to nasally-administered vaccine compositions effective in naive subjects such as children. Further, the vaccine composition is suitable for vaccinating the general population during a pandemic.

BACKGROUND OF THE INVENTION

Influenza vaccines currently in general use are based on live virus or inactivated virus, and inactivated virus vaccines can be based on whole virus, "split" virus, subunit proteins or on purified surface antigens (including haemagglutinin and neuraminidase).

The socioeconomic impact of influenza and its medical burden in healthy young children has been increasingly recognized. Moreover, children have the highest attack rates of influenza during epidemic periods, and transmit influenza viruses in the community to other risk groups.

Healthy young children have an increased risk of influenza infection because they do not have a fully developed immune system. Infants are in their first three months of life susceptible to infections that are not common in older individuals (such as *Streptococcus agalactiae*) and infants rely on maternal antibody for the first few month of life. Infants do not respond to certain vaccines in the same way as adults and are unable to produce effective antibodies to polysaccharide antigens until around 5 years of age. The immune system grows and develops with the child and does not fully resemble that of an adult until puberty, when sex hormones may be responsible for the full maturation of the child's immune system.

The American Advisory Committee on Immunization Practices (ACIP) has recommended annual influenza vaccination for all children aged 6-59 months, because children aged 6-23 months are at substantially increased risk for influenza-related hospitalizations and children aged 24-59 months are at increased risk for influenza-related clinic and emergency department visits. The recommendation has been extended for seasonal influenza vaccination for all persons aged ≥6 months who do not have contraindications. The U.S. food and drug administration categorizes pediatric subpopulation according to the following age ranges. The newborn population range from birth to 1 month of age. The infant population range from 1 month to 2 years of age. The child population range from 2 years to 12 years of age. The adolescent population range from 12 to 21 years of age. In Europe, some countries have issued similar recommendations as the ACIP, although with a more restricted position with regard to universal immunization of young children. The European Medicines Agency categorizes paediatric medicines according to the following populations. The newborn population includes pre-term to term and up to 28 days. The infant population are from 1 month to 23 months. The child population are form 2 years to 11 years. Adolescents are from 12 years to 18 years.

Studies have shown that conventional parenteral vaccines have limited ability to induce satisfactory protective immunity in unprimed (naïve) children, especially the very young ones. ACIP has recommended a two-dose vaccination regimen in immunologically naive very young children, but more recently such recommendation has been extended to children aged up to 8 years of age, because of the accumulating evidence indicating that 2 doses are required for protection in this population.

During inter-pandemic periods, influenza viruses that circulate are related to those from the preceding epidemics. The viruses spread among people with varying levels of immunity from infections earlier in life. Such circulation, in a phenomenon known as antigenic drift, over a period of usually 2-3 years, promotes the selection of new strains that have changed enough to cause an epidemic again among the general population. Drift variants may have different impacts in different communities, regions, countries or continents in any one year, although over several years their overall impact is often similar. Typical influenza epidemics cause increases in incidence of pneumonia and lower respiratory disease as witnessed by increased rates of hospitalisation and mortality.

At unpredictable intervals, novel influenza viruses emerge through a process known as "antigenic shift" and are able to cause pandemics. Antigenic shift is the process by which two or more different strains of a virus combine to form a new subtype having a mixture of the surface antigens of the two or more original strains. Antigenic shift is a specific case of reassortment or viral shift that confers a phenotypic change. Thus, an influenza pandemic occurs when a new influenza virus appears against which the human population has no pre-existing immunity. The general population will when an antigenic shift occurs be naive to the new virus strain.

Antigenic shift is contrasted with antigenic drift, which is the natural mutation over time of known strains of influenza which may lead to a loss of immunity, or in vaccine mismatch. Antigenic drift occurs in all types of influenza including influenza virus A, influenza B and influenza C. Antigenic shift, however, occurs only in influenza virus A because it infects more than just humans.

During a pandemic, antiviral drugs will not be sufficient or effective enough to cover the needs and the number of individuals at risk of potentially life-threating influenza disease. The development of suitable vaccines is essential in order to achieve protective antibody levels in immunologically naive subjects.

These problems may be countered by adjuvantation and/or optimal vaccine delivery the aim of which is to increase immunogenicity of the vaccine in order to be able to decrease the antigen content and thus increase the number of vaccine doses available. The use of an adjuvant may also help prime the immune system against an antigen in a population with no pre-existing immunity to the specific influenza strain. An adjuvant may also enhance the delivery of the vaccine and thereby decrease the amount of antigen needed to induce an immune response. The vaccine delivery and/or the route of vaccination might be of high importance. Most influenza vaccines are delivered parenterally and therefore mainly induce immunity against influenza in the blood. However, influenza viruses enter our bodies through our nose or mouth i.e. through mucosal membranes. By delivering influenza vaccine to the nose one can induce influenza-specific immunity in both the mucosa and in the blood. This might be of benefit when aiming to induce protective immunity against influenza, especially in individuals with no prior immunity to the influenza vaccine strain or to any influenza.

New non-live vaccines, such as a vaccine based on a whole inactivated virus or on part from an inactivated virus, able to induce protective immunity against influenza disease in individuals with no pre-existing immunity to the vaccine antigen are needed. Individuals without sufficient pre-existing immunity to influenza and/or with weakened immune status include immuno-compromised individuals, young children, elderly and large parts of the world wide population (or all) in case of a pandemic. The present invention is directed particularly to children with limited or no pre-existing immunity to viral antigens. This group especially is in need of a safe, non-live vaccine that can prime an immunological response against e.g. influenza. New vaccines that could be used as peri-pandemic vaccines to prime an immunologically naive population against a pandemic strain before or upon declaration of a pandemic are also needed. The present invention is directed particularly to naive populations and notably can be readily administered due to being formulated for nasal administration and only containing inactivated virus or parts of viruses, thus not requiring medically trained personnel. Formulations of vaccine antigens with potent adjuvants allow for enhancing immune responses.

SUMMARY OF THE INVENTION

It is an object of the invention to provide vaccines that are able to prime an immune response and provide protective immunity against both seasonal and pandemic virus strains and other pathogenic organisms in subjects with no pre-existing immunity to the vaccine strain. One aspect of the invention is directed to the paediatric use of the vaccine of the invention including a vaccine effective in children against seasonal influenza virus strains. A further aspect of the invention is directed to subjects of all age groups when the composition is for pandemic use.

A first aspect of the present invention is directed to a composition comprising
  i) one or more non-live antigens, and
  ii) an adjuvant comprising:
  one or more carboxylic acids,
  an aqueous medium, and
  optionally one or more mono-glycerides
for use as an intranasally administered vaccine for use in naive subjects.

The composition may be formulated for use as a vaccine against all suitable pathogens. Thus the composition may be formulated as a vaccine for any suitable viral strain or bacteria. The composition may be formulated for use as an influenza vaccine for intranasal administration. The invention was developed for use as a vaccine for the intranasal immunization against pathogenic infections e.g. influenza in subjects with limited or no pre-existing immunity to the vaccine strain.

A second aspect of the present invention is directed to a composition for use as an intranasally administered vaccine to pediatric immuno-compromised subjects, the composition comprising
  one or more non-live influenza virus antigens, and
  an adjuvant comprising:
  one or more carboxylic acids,
  an aqueous medium, and
  optionally one or more mono-glycerides.

A third aspect of the invention is directed to a composition comprising
  i) one or more non-live antigens, and
  ii) an adjuvant comprising:
  one or more carboxylic acids,
  an aqueous medium, and
  optionally one or more mono-glycerides
for use as an intranasally administered vaccine for use in naive immuno-compromised patients.

A further aspect of the invention is directed to a composition, said composition comprising
  i) one or more *Streptococcus pneumoniae* antigens, and
  ii) an adjuvant comprising:
  one or more carboxylic acids,
  an aqueous medium, and
  optionally one or more mono-glycerides
for use as an intranasally administered vaccine for use in naive subjects and/or immune-compromised patients for the prevention of infection with *Streptococcus pneumoniae* or for reducing the severity of symptoms associated with an infection with *Streptococcus pneumoniae*

BRIEF DESCRIPTION OF THE DRAWINGS

Ferrets of group 1, 3-6 were intranasally inoculated by nasal drops on days 0, 21 and 42 and ferrets of group 2 were subcutaneously injected on days 21 and 42. HI antibody titers were determined in sera collected prior to the immunizations on day 0, 21 and 42 and after the last immunization on days 64 and 70. Group 1 (control, i.n. saline), group 2 (s.c. TIV), group 3 (i.n. Endocine™ adjuvanted split antigen at 5 µg HA), group 4 (i.n. Endocine™ adjuvanted split antigen at 15 µg HA), group 5 (i.n. Endocine™ adjuvanted split antigen at 30 µg HA) and group 6 (i.n. Endocine™ adjuvanted inactivated whole virus antigen at 15 µg HA). Bars represent geometric mean of 6 animals per group with 95% CI (GMT+/−0195). For GMT calculations, the ≤5 value was replaced with the absolute value 5. FIG. 2A: Antibody titers against H1N1 A/Swine/Ned/25/80. FIG. 2B: Antibody titers against H1N1 A/Swine/Italy/14432/76. FIG. 2C: Antibody titers against H1N1 A/New Jersey/08/76.

Figure 1:
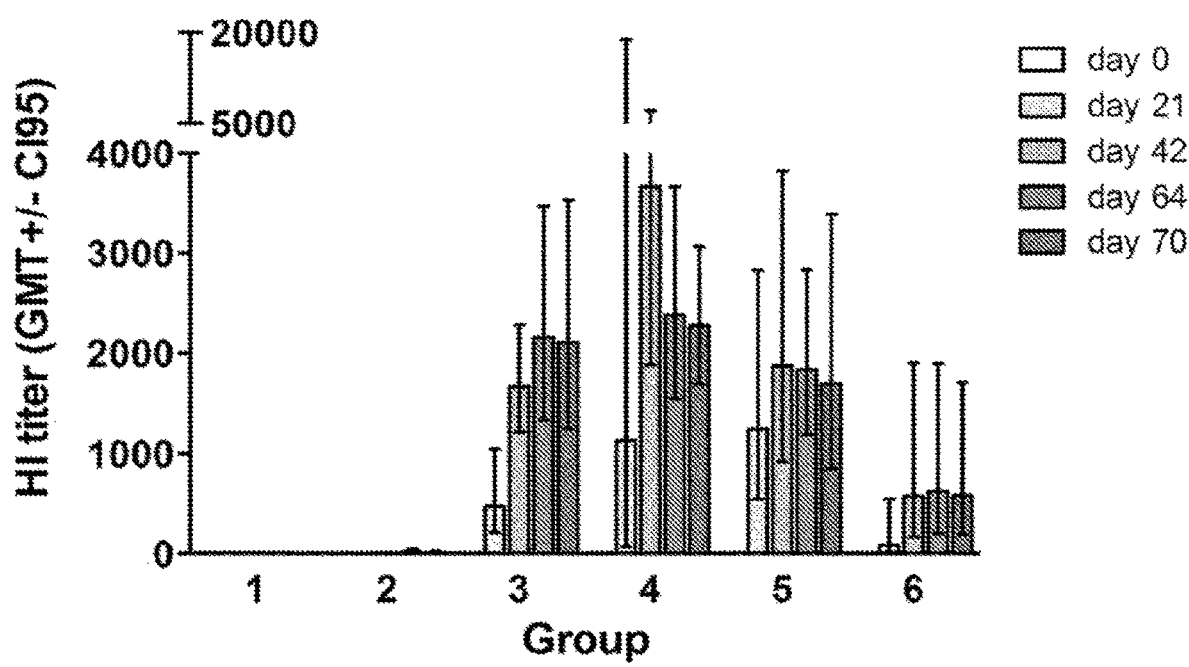
FIG. 1: Development of HI antibody titers against H1N1 A/Ned/602/09 (A). Ferrets of group 1, 3-6 were intranasally inoculated by nasal drops on days 0, 21 and 42 and ferrets of group 2 were subcutaneously injected on days 21 and 42. HI antibody titers were determined in sera collected prior to the immunizations on day 0, 21 and 42 and after the last immunization on days 64 and 70. Group 1 (control, i.n. saline), group 2 (s.c. TIV), group 3 (i.n. Endocine™ adjuvanted split antigen at 5 µg HA), group 4 (i.n. Endocine™ adjuvanted split antigen at 15 µg HA), group 5 (i.n. Endocine™ adjuvanted split antigen at 30 µg HA) and group 6 (i.n. Endocine™ adjuvanted inactivated whole virus antigen at 15 µg HA). Bars represent geometric mean of 6 animals per group with 95% CI (GMT+/−0195).

Ferrets of group 1, 3-6 were intranasally inoculated by nasal drops on days 0, 21 and 42 and ferrets of group 2 were subcutaneously injected on days 21 and 42. VN antibody titers were determined in sera collected prior to the immunizations on day 0, 21 and 42 and after the last immunization on days 64 and 70. Group 1 (control, i.n. saline), group 2 (s.c. TIV), group 3 (i.n. Endocine™ adjuvanted split antigen at 5 µg HA), group 4 (i.n. Endocine™ adjuvanted split antigen at 15 µg HA), group 5 (i.n. Endocine™ adjuvanted split antigen at 30 µg HA) and group 6 (i.n. Endocine™ adjuvanted inactivated whole virus antigen at 15 µg HA). Bars represent geometric mean of 6 animals per group with 95% CI (GMT+/−CI95).

Figure 4:
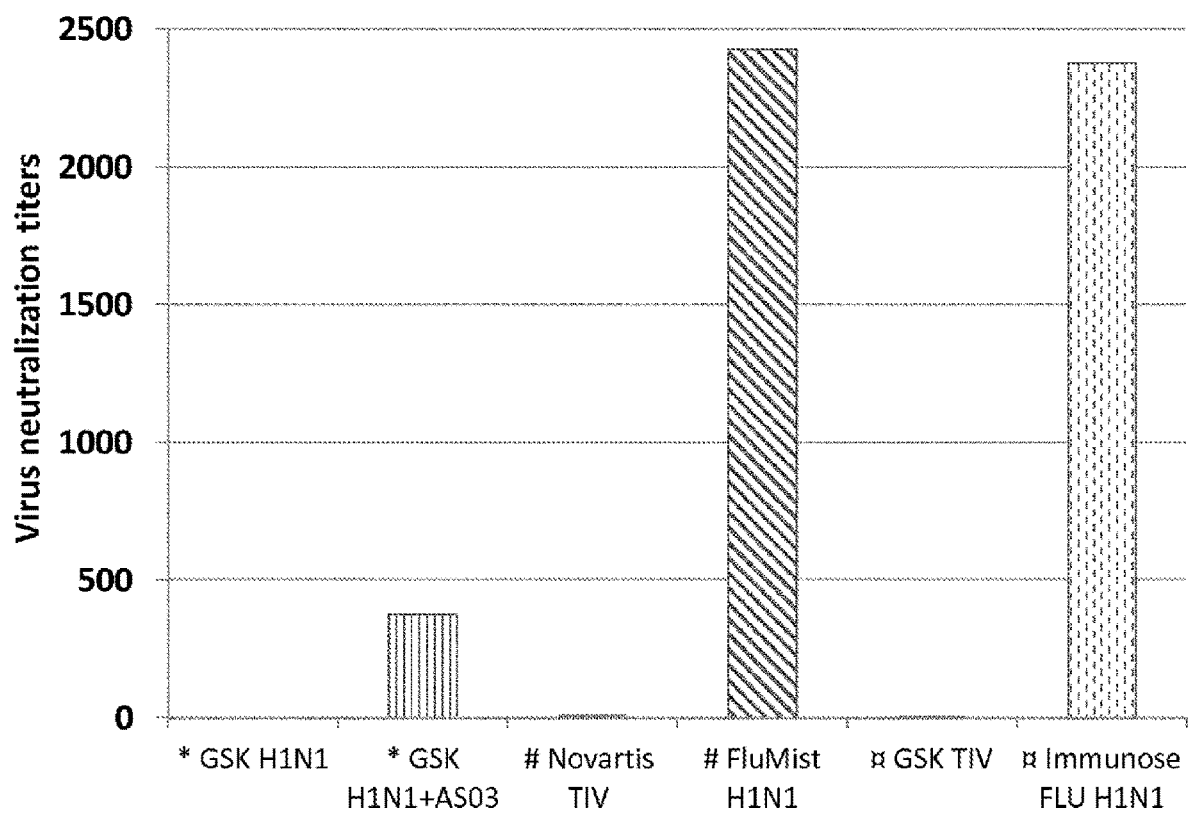

FIG. 4: Comparison of the vaccine Immunose™ FLU, here comprising 15 ug HA split influenza antigen with 20 mg/ml (2%) Endocine™, of the present invention with other adjuvanted vaccine products, FluMist (live attenuated vaccine) and injectable vaccines in influenza naïve ferrets.

FIG. 5 depicts Table 3: Efficacy of Endocine™ formulated 2009 H1N1 vaccines in ferrets demonstrated by clinical, virological and gross-pathology parameters.

Group 1 (control, i.n. saline), group 2 (s.c. TIV), group 3 (i.n. Endocine™ adjuvanted split antigen at 5 µg HA), group 4 (i.n. Endocine™ adjuvanted split antigen at 15 µg HA), group 5 (i.n. Endocine™ adjuvanted split antigen at 30 µg HA) and group 6 (i.n. Endocine™ adjuvanted inactivated whole virus antigen at 15 µg HA).

Clinical Scores. Survival, number of animals that survived up to 4 dpi; fever (° C.), maximum temperature increase presented as average with standard deviation, number of animals in which fever was observed in parentheses, (*), body temperature of 1 animal in group 4 was not available due to malfunction of the recorder; % body weight loss between 0 and 4 dpi presented as average with standard deviation, number of animals with body weight loss in parentheses.

Virology. Virus shedding in nose and throat swab samples, area under the curve (AUC) for titration results 1-4 dpi, number of animals showing 1 or more virus positive swab in parentheses; virus load in lung and turbinates ($\log_{10}TCID_{50}$/g) on 4 dpi presented as average with standard deviation, or the lower limit of detection in case all animals in the group were virus negative, number of animals with lung/turbinate virus in parentheses.

Gross pathology. % of estimated affected lung parenchyma by visual examination during necropsy on 4 dpi presented as average with standard deviation, number of animals with affected lung in parentheses; lung/body weight ratio ($\times 10^2$) on 4 dpi presented as average with standard deviation.

FIG. 6 depicts Table 4: Semi-quantitative scoring for histopathological parameters on 4 dpi.

$^a$: Group 1 (control, i.n. saline), group 2 (s.c. TIV), group 3 (i.n. Endocine™ adjuvanted split antigen at 5 µg HA), group 4 (i.n. Endocine™ adjuvanted split antigen at 15 µg HA), group 5 (i.n. Endocine™ adjuvanted split antigen at 30 µg HA) and group 6 (i.n. Endocine™ adjuvanted inactivated whole virus antigen at 15 µg HA).

Histopathology. Semi-quantitative scoring for histopathological parameters on 4 dpi. Extent of alveolitis/alveolar damage, score: 0, 0%; 1, 25%; 2, 25-50%; 3, >50%; severity of alveolitis, score: no inflammatory cells (0); few inflammatory cells (1); moderate numbers of inflammatory cells (2); many inflammatory cells (3); alveolar oedema, alveolar haemorrhage and type II pneumocyte hyperplasia were scored as positive slides (no=0, yes=1); All histopathology results are presented as average with standard deviation.

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

The term "naïve subjects" means subjects immunologically naïve to a pathogen i.e. subjects that have not been vaccinated or exposed to a given pathogen and therefore has no pre-existing immunity to that pathogen.

The term "influenza naive subjects" means subjects immunologically naïve to a specific influenza virus i.e. subjects that have not been vaccinated or exposed to a specific influenza and therefore has no pre-existing immunity to that influenza strain. For influenza it means infants and children when vaccinating against seasonal influenza and means entire populations when peri-pandemic and pandemic periods, including infants, children, adults, and the elderly.

The term "pediatric subjects" refers to children under the age of 21 and include the following subpopulations newborn population from the day of birth to 1 month of age, infants from 1 month to 2 years of age, child from 2 years to 12 years of age and adolescent from 12 years to 21 years of age.

The term "peri-pandemic period" refers to the time period surrounding a pandemic. Given pandemics are time periods officially identified by WHO, the term refers to the time period immediately prior to the official recognition of the pandemic and immediately following a pandemic, during which time vaccination is recommended.

The term "non-live antigens" refers to antigens derived from inactivated, non-live pathogens including viruses e.g. whole inactivated viruses, split antigens, subunit antigens, recombinant antigens or peptides or bacteria or parasites.

The term "Immunose™ FLU" refers to a composition comprising non-live influenza antigen and Endocine™.

The term "Endocine™" refers to an adjuvant comprising equimolar amounts of glycerol monooleate and oleic acid The one or more non-live influenza virus antigens in the composition of the invention can be from one or more influenza strain, A, B and/or C strain. A vaccine composition that is able to prime an immune response and provide protective immunity against pandemic influenza strains normally only contains antigens from one influenza A strain (monovalent) whereas a vaccine composition that is able to prime an immune response and provide protective immunity against seasonal influenza strains normally contains antigens from three or more different strains (trivalent or quadrivalent). Most commonly two different influenza A strains and one or more influenza B strains.

The invention is directed to a vaccine composition surprisingly found to be highly effective against subjects naive to influenza viral strains, such as children (younger than 8 years old) and persons during a peri-pandemic or pandemic period. Children are often naive to influenza strains circulating seasonally whereas all persons are considered naive during a pandemic.

The invention is further directed to a method of immunization before or during an epidemic or pandemic period comprising intranasally administering a vaccine composition comprising a composition of the invention as well as to a method of immunization of paediatric subjection comprising intranasally administering a vaccine composition comprising a composition of the invention and still further directed to a method of immunization of naïve subjects comprising intranasally administering a vaccine composition comprising a composition of the invention.

The invention is directed to infants, children and adolescent populations as these populations, when naïve, are less responsive when it comes to common vaccine strategies. The immune system in infants and children are not fully developed and they therefore mount a less efficient immune response to conventional parenteral vaccine strategies. However, the present invention offers a special opportunity for infants and children as a unique lymphoid tissue in the upper respiratory tract is present at birth and well developed early in childhood. The pharyngeal lymphoid tissue known as the adenoid (or nasopharyngeal tonsil) is located in the pharynx of children and is part of Waldeyer's ring which comprises the nasopharyngeal tonsil (adenoid(s)), the pair of palatine tonsils, the pair of tubal tonsils and the lingual tonsils. The adenoid is active in building up the immune system and starts to disappear during adolescence. Nasal vaccine delivery may therefore be of particular advantages for infants and children. Pediatric subpopulations may be defined either as by the U.S. Food and Drug Administration or as by the European Medicines Agency or as a combination of the two.

In one embodiment the composition is for use as an intranasal administered vaccine for pediatric use. In one embodiment the composition is for use as an intranasal administered vaccine in newborn ((term and pre-term) with an age up to 28 days). In one embodiment the composition is for use as an intranasal administered vaccine in infants (with an age of 1 month to 23 months). In one embodiment the composition is for use as an intranasal administered vaccine in children (with an age of 2 years to 11 years). In one embodiment the composition is for use as an intranasal administered vaccine in adolescent (with an age of 12 years to 18 years).

There is a need for a safe vaccine suitable for small children with limited or no pre-existing immunity to e.g. influenza and for naive subjects in general that induces protective immunity against e.g. influenza disease.

Live attenuated virus vaccines are associated with safety concerns. Flumist® has not been approved, due to these safety issues, for use in small children under 2 years of age. Paradoxically, these are most often naive subjects which are particularly vulnerable to influenza, and belong to a high risk group for influenza. Flumist® is approved for older children but is a live attenuated virus vaccine.

It has surprisingly been found that intranasal administration of adjuvanted non-live influenza vaccines induced very high immune responses and subsequent complete protection against influenza disease in ferrets with no pre-existing immunity to the vaccine antigen. Both the whole and split non-live antigen vaccines gave superior results over the injected commercially available influenza vaccine, Fluarix®.

The composition of the invention does not utilize a live attenuated virus but rather non-live influenza virus antigens. Moreover, it can be administered intranasally. Intranasal administration is particularly suitable for pediatric administration in infants and children due to the presence of the pharyngeal lymphoid tissue known as the adenoid. The intranasal administration of the composition of the invention allows for its generalized use and administration without specialized training, such as throughout the population during pen-pandemic and pandemic periods by self-administration. The use of non-live influenza virus antigens allows for its use in small children without the safety concerns associated with live attenuated virus vaccines. The inventors have developed a vaccine efficacious in naive subjects which may be intranasally administered, thereby having the above-mentioned advantages and meeting an important need for vulnerable populations and classes of patients.

The invention is directed, in a first aspect, to a composition, said composition comprising i) one or more non-live antigens, and ii) an adjuvant comprising:

one or more carboxylic acids, an aqueous medium, and optionally one or more mono-glycerides for use as an intranasally administered vaccine for use in naive subjects.

In another aspect the invention is directed to a composition comprising i) one or more non-live virus antigens, and ii) an adjuvant comprising:

one or more carboxylic acids, an aqueous medium, and optionally one or more mono-glycerides for use as an intranasally administered vaccine for use in naive subjects.

The composition of the invention is suitable for use as a vaccine against infectious pathogens e.g. virus and bacteria. The composition of the invention is suitable for an influenza vaccine for intranasal administration. The composition of the invention is directed for use as a vaccine for the intranasal immunization against influenza in naïve subjects.

The influenza viruses consist of three types A, B, and C. Influenza A viruses infect a wide variety of birds and mammals, including humans, horses, pigs, ferrets, and chickens. Influenza B is present in humans, ferrets and seals and influenza C is present in humans dogs and pigs. Animals infected with Influenza A often act as a reservoir for the influenza virus, by generating pools of genetically and antigenically diverse viruses which are transmitted to the human population. Transmission may occur through close contact between humans and the infected animals, for example, by the handling of livestock. Transmission from human to human may occur through close contact, or through inhalation of droplets produced by coughing or sneezing.

The outer surface of the influenza A virus particle consists of a lipid envelope which contains the glycoproteins hemagglutinin (HA) and neuraminidase (NA). The HA glycoprotein is comprised of two subunits, termed HA1 and HA2. HA contains a sialic acid binding site, which binds to sialic acid found on the outer membrane of epithelial cells of the upper and lower respiratory tract, and is absorbed into the cell via receptor mediated endocytosis. Once inside the cell, the influenza virus particle releases its genome, which enters the nucleus and initiates production of new influenza virus particles. NA is also produced, which cleaves sialic acid from the surface of the cell to prevent recapture of released influenza virus particles. The virus incubates for a short period, roughly five days in a typical case, although the incubation period can vary greatly. Virus is secreted approximately one day prior to the onset of the illness, and typically lasts up to three to five days. Typical symptoms include fever, fatigue, malaise, headache, aches and pains, coughing, and sore throat. Some symptoms may persist for several weeks post infection.

Different strains of influenza virus are characterized primarily by mutations in the HA and NA glycoproteins, and thus HA and NA are used to identify viral subtypes (i.e., H5N1 indicates HA subtype 5 and NA subtype 1). As such, influenza vaccines often target the HA and NA molecules. Conventional influenza virus vaccines often utilize whole inactivated viruses, which possess the appropriate HA and/or NA molecule. Alternatively, recombinant forms of the HA and NA proteins or their subunits may be used as vaccines. The antigen in the vaccine composition may be inactivated antigens such as e.g. whole inactivated viruses, split antigens, subunit antigens, recombinant antigens or peptides. The term "antigen" or "immunogen" is defined as anything that can serve as a target for an immune response. The term also includes protein antigens, recombinant protein components, virus like particles (VLPs) as well as genetically engineered RNA or DNA, which—when injected into the cells of the body—the "inner machinery" of the host cells "reads" the DNA and uses it to synthesize the pathogen's proteins. Because these proteins are recognised as foreign, when they are processed by the host cells and displayed on their surface, the immune system is alerted, which then triggers a range of immune responses. The term also includes material, which mimic inactivated bacteria or viruses or parts thereof. The immune response can be cellular and/or humoral and be detected in systemic and/or mucosal compartments.

However, influenza is an RNA virus and is thus subject to frequent mutation, resulting in constant and permanent changes to the antigenic composition of the virus. The antigenic composition refers to portions of the polypeptide which are recognized by the immune system, such as antibody binding epitopes. Small, minor changes to the antigenic composition are often referred to as antigenic drift. Influenza A viruses are also capable of "swapping" genetic materials from other subtypes in a process called reassortment, resulting in a major change to the antigenic composition referred to as antigenic shift. Because the immune response against the viral particles relies upon the binding of antibodies to the HA and NA glycoproteins, frequent changes to the glycoproteins reduce the effectiveness of the immune response acquired against influenza viruses over time, eventually leading to a lack of immunity. The ability of influenza A to undergo a rapid antigenic drift and shift can often trigger influenza epidemics due to the lack of pre-existing immunity to the new strain.

The American Advisory Committee on Immunization Practices (ACIP) has recommended annual influenza vaccination for all children aged 6-59 months, because children aged 6-23 months are at substantially increased risk for influenza-related hospitalizations and children aged 24-59 months are at increased risk for influenza-related clinic and emergency department visits. The recommendation has been extended for seasonal influenza vaccination to all persons ages ≥6 months. Accordingly, the composition of the invention is for use as a vaccine for intranasal administration to children aged 18 years and under, particular aged 12 and under. Typically, the children are less than 8 years of age, such as 6 years old or less. An important intended class of patients for the vaccine of the invention is children, particularly children of 2 months to less than 9 years of age, typically children of age 3 months to less than 9 years old, such as of age 6 months to less than 8 years old, most typically of age 6 month to less than 7 years old, such as of age 6 months to less than 72 months, or of age 6 months to 60 months, or of age 6 months to 24 months. The composition of the invention is intended, at least in part, as a vaccine for paediatric use.

The features of an influenza virus strain that give it the potential to cause a pandemic outbreak are: it contains a new haemagglutinin compared to the haemagglutinin in the recently circulating strains, which may or may not be accompanied by a change in neuraminidase subtype; it is capable of being transmitted horizontally in the human population; and it is pathogenic for humans. A new haemagglutinin may be one which has not been evident in the human population for an extended period of time, probably a number of decades, such as H2. Or it may be a haemagglutinin that has not been circulating in the human population before, for example H5, H9, H7 or H6 which are found in birds. In either case the majority, or at least a large proportion of, or even the entire population has not previously encountered the antigen and is immunologically naive to it.

The invention is directed to infants, children and adolescent populations as these populations, when naive, are less responsive when it comes to common vaccine strategies. The immune system in infants and children are not fully developed and they therefore mount a less efficient immune response to conventional parenteral vaccine strategies. However, the present invention offers a special opportunity for infants and children as a unique lymphoid tissue in the upper respiratory tract is present at birth and well developed early in childhood. The pharyngeal lymphoid tissue known as the adenoid (or nasopharyngeal tonsil) is located in the pharynx of children and is part of Waldeyer's ring which comprises the nasopharyngeal tonsil (adenoid(s)), the pair of palatine tonsils, the pair of tubal tonsils and the lingual tonsils. The adenoid is active in building up the immune system and starts to disappear during adolescence. Nasal vaccine delivery may therefore be of particular advantages for infants and children. Pediatric subpopulations may be defined either as by the U.S. Food and Drug Administration or as by the European Medicines Agency or as a combination of the two.

The U.S. food and drug administration categorizes pediatric subpopulation according to the following age ranges. The newborn population range from birth to 1 month of age. The infant population range from 1 month to 2 years of age. The child population range from 2 years to 12 years of age. The adolescent population range from 12 to 21 years of age. The European Medicines Agency categorizes paediatric medicines according to the following populations. The newborn population includes pre-term to term and up to 28 days. The infant population are from 1 month to 23 months. The child population are form 2 years to 11 years. Adolescents are from 12 years to 18 years.

In one embodiment the composition is for use as an intranasal administered vaccine for pediatric use. In one embodiment the composition is for use as an intranasal administered vaccine in newborn ((term and pre-term) with an age up to 28 days) or alternatively for use in newborn from day of birth to an age of 1 month. In one embodiment the composition is for use as an intranasal administered vaccine in infants with an age of 1 month to 23 months or alternatively with an age of 1 month to 2 years. In one embodiment the composition is for use as an intranasal administered vaccine in children with an age of 2 years to 11 years or alternatively with an age of 2 years to 12 years. In one embodiment the composition is for use as an intranasal administered vaccine in adolescent with an age of 12 years to 18 years alternatively with an age of 12 years to 21 years.

The vaccine of the invention is particularly directed to naive subjects, eg children below 8 years of age during seasonal influenza epidemics. The composition of the invention is also intended, as a vaccine for use in all age groups during pandemic or peri-pandemic periods.

The composition is therefore particularly directed to naive subjects. The naive subjects may be children under 18 years old, such as children 0 to 18 years, particularly children aged 12 and under. Typically, the children are less than 8 years of age, such as 6 years old or less. An important intended class of patients for the vaccine of the invention is particularly children of 2 months to less than 9 years of age, typically children of age 3 months to less than 9 years old, such as of age 6 months to less than 8 years old, most typically of age 6 month to less than 7 years old, such as of age 6 months to less than 72 months, or of age 6 months to 60 months or of age 6 months to 24 months. The composition of the invention is intended, at least in part, as a vaccine for pediatric use.

The naive subjects may be of all age groups when the composition is particularly directed to a vaccine for use during pandemic or pen-pandemic periods.

Intranasal administration is intended to mean administration to the nose by any mode of administration such as by spraying the vaccine into the nasal cavity or by administering the vaccine via pipette or similar device by dripping the vaccine into the nasal cavity or onto the nasal mucosal wall.

The composition advantageously comprises one or more non-live influenza virus antigens rather than live attenuated virus. As stated, this avoids safety concerns both in the selection of the patient class but also in terms of production, distribution, nasal administration, handling and disposal. The non-live influenza virus antigen may be selected from the group consisting of whole inactivated virus, split virus, subunit influenza antigen and recombinant antigens. The use of recombinant proteins can be used to increase the titer of neutralizing antibodies produced against a challenge with the virus. The glycosylation of HA plays an important role in the ability of the immune response to elict an antibody response and the virus ability to evade the immune system. Hence recombinant HA proteins can be generated containing heterogeneous complex-type glycans as well as recombinant proteins which are monoglycosylated or non-glycosylated with increased immunogenicity.

Preferably, the non-live influenza virus antigen is a split antigen or a subunit influenza antigen, more preferably a split antigen.

The influenza A genome contains 11 genes on eight pieces of RNA, encoding for 11 proteins: hemagglutinin (HA), neuraminidase (NA), nucleoprotein (NP), M1, M2, NS1, NS2 (NEP: nuclear export protein), PA, PB1 (polymerase basic 1), PB1-F2 and PB. Non-live influenza virus antigens may be selected from any one protein or combination of proteins from the virus.

The composition of the invention may comprise any inactivated influenza virus. As understood by the person skilled in the art, the influenza virus varies from season to season and also by geographic area and populations in which they infect. The present invention is directed to vaccines comprising an adjuvant of the invention and non-live influenza virus antigens from one or more influenza virus. The non-live influenza antigen used in the vaccine composition of the invention will be any antigenic material derived from an inactivated influenza virus. For instance, it may comprise inactivated whole virus particles. Alternatively, it may comprise disrupted virus (split virus) wherein for instance an immunogenic protein, for example M2 ion channel protein, or glycoproteins are retained. Purified preparations of influenza membrane glycoproteins, haemagglutinin (HA) and/or neuraminidase (NA) may be used as the antigenic material in the vaccine composition. A vaccine composition according to the invention may comprise one or more types of antigenic materials. The influenza type virus used to prepare the vaccine composition will, of course, depend on the influenza against which a recipient of the vaccine is to be protected.

For example, the non-live influenza virus antigen comprises one or more antigens of, for instance, the genetic backbone of one or more of the following influenza viruses: A/Ann Arbor/6/60 (A/AA/6/60), B/Ann Arbor/1/66 virus, the FluMist MDV-A (ca A/Ann Arbor/6/60), the FluMist MDV-B (ca B/Ann Arbor/1/66), A/Leningrad/17 donor strain backbone, and PR8.

In another specific example, the vaccine compositions of the invention comprise a non-live influenza virus antigen of, for instance, an HA or an NA polypeptide sequence (or at least 90% identical or at least 95% identical to such sequences) from one or more of the following: B/Yamanashi; A/New Caledonia; A/Sydney; A/Panama; B/Johannesburg; B/Victoria; B/Hong Kong; A/Shandong/9/93; A/Johannesburg/33/94; A/Wuhan/395/95; A/Sydney/05/97; A/Panama/2007/99; A/Wyoming/03/2003; A/Texas/36/91; A/Shenzhen/227/95; A/Beijing/262/95; A/New Caledonia/20/99; B/Ann Arbor/1/94; B/Yamanashi/166/98; B_Johannesburg.sub.--5.sub.--99; BVictoria/504/2000; B/Hong Kong/330/01; B_Brisbane.sub.--32.sub.--2002; B/Jilin/20/03; an H1N1 influenza A virus, an H3N2 influenza A virus, H9N2 influenza A virus, an H5N1 influenza A virus, an H7N9 influenza A virus; an influenza B virus; and a pandemic influenza strain (either designated by WHO or not circulating in the human population).

In one embodiment the influenza virus strain may be of one or more of the strains included in the 2013/2014 vaccine: such as an A/California/7/2009 (H1N1)-like virus, an (H3N2) virus antigenically like the cell-propagated prototype virus A/Victoria/361/2011 or A/Texas/50/2012 and a B/Massachusetts/2/2012-like (Yamagata lineage) virus.

In one embodiment the influenza virus strain may be of one or more of the strains previously recommended by the WHO for use in an influenza vaccine.

In one embodiment the influenza virus strain or strains may be a strain from a Quadrivalent influenza vaccine and contain antigens from any four of the following five influenza virus strains; an A/California/7/2009 (H1N1)-like virus, an (H3N2) virus antigenically like the cell-propagated prototype virus A/Victoria/361/2011 or A/Texas/50/2012 and a B/Massachusetts/2/2012-like (Yamagata lineage) virus, a B/Brisbane/60/2008-like (Victoria lineage) virus.

The adjuvant of the composition of the invention is critical for its suitability for intranasal administration and for its efficacy. A suitable adjuvant for intranasal administration may be an adjuvant that comprises optionally a monoester of glycerol in combination with a fatty acid, or it may be a combination of fatty acids. Carboxylic acids used in such adjuvants comprise long chain (C4-C30) alkyl, alkenyl or alkynyl carboxylic acids which may optionally be branched or unbranched, cyclic or acyclic, optionally having single, double or multiple unsaturation (double or triple bond) which may further optionally be of different kind.

Monoglycerides used in such adjuvants may be carboxylic acid esters of glycerin, wherein the carboxylic acids may be long chain (C4-C30) alkyl, alkenyl or alkynyl carboxylic acids which may optionally be branched or unbranched, optionally having single, double or multiple unsaturation (double or triple bond) which may further optionally be of different kind.

The concentration of monoglyceride in a vaccine composition may be in the range of e.g. about 1 to about 50 mg/ml, such as, e.g. from about 1 to about 25 mg/ml, from about 5 to about 15 mg/ml or about 10 mg/ml.

The concentration of fatty acid in a vaccine composition may be in the range of e.g. about 0.5 to about 50 mg/ml, such as, e.g. from about 1 to about 25 mg/ml, from about 1 to about 15 mg/ml, from about 1 to about 10 mg/ml, from about 2 to about 8 mg/ml or about 6-7 mg/ml. In one embodiment the molar basis of the concentration of a fatty acid in the vaccine composition corresponds to the concentration (on a molar basis) of the monoglyceride.

Any combination of the concentration ranges mentioned above for monoglyceride and fatty acid is within the context of the present application. Moreover, the broadest range mentioned gives a preferred range, and then the range is narrowed to the most preferred range.

The inventors of the present invention have found that adjuvants as described above and disclosed in WO 2012/042003 (which is hereby included in its entirety by reference) are particularly useful when vaccination is performed via the nasal route, e.g. administration to the mucosa of the nasal cavity. The inventors have found that use of such adjuvants in vaccination via the nasal route improves the immune response upon vaccination. The inventors have found the use of such adjuvants safe and tolerable in several species including humans.

Accordingly, the composition may comprise mono-glycerides which are glycerides mono-esterified with carboxylic acids selected from the group consisting of lauric acid (C12), myristic acid (C14), palmitic acid (C16), palmitoleic acid (C16:1), oleic acid (C18:1), linoleic acid (C18:2), stearic acid, hexanoic acid, caprylic acid, decanoic acid (capric acid), arachidic acid, behenic acid, lignoceric acid, alpha-linolenic acid, stearidonic acid, eicosapentaenoic acid, docosahexaenoic acid, gamma-linolenic acid, dihomo-gamma-linolenic acid, arachidonic acid, erucic acid, nervonic acid.

In a further embodiment, the mono-glycerides are glycerides mono-esterified with carboxylic acids selected from the group consisting of palmitoleic acid (C16:1), oleic acid (C18:1) and linoleic acid (C18:2).

Preferably, the mono-glyceride is glyceride mono-esterified with oleic acid (glyceryl oleate).

The adjuvant preferably comprises one or more carboxylic acids selected from the group consisting of lauric acid, myristic acid, palmitic acid, palmitoleic acid, oleic acid, linoleic acid stearic acid, hexanoic acid, caprylic acid, decanoic acid (capric acid), arachidic acid, behenic acid, lignoceric acid, alpha-linolenic acid, stearidonic acid, eicosapentaenoic acid, docosahexaenoic acid, gamma-linolenic acid, dihomo-gamma-linolenic acid, arachidonic acid, erucic acid and nervonic acid. Preferably, the one or more carboxylic acids are selected from the group consisting of oleic acid and lauric acid.

In a combination of suitable embodiments, the adjuvant comprises glyceryl oleate, oleic acid and an aqeuous medium. The vaccine composition of the present invention can also comprise additional pharmaceutical excipients. Such pharmaceutical excipients can be:

1. Agents to control the tonicity/osmolarity of the vaccine. Such agents are e.g. physiological salts like sodium chloride. Other physiological salts are potassium chloride, potassium dihydrogen phosphate, disodium phosphate, magnesium chloride etc. Such agent could also be other ionic substances which influence the ionic strength and stability. The osmolality of the vaccine may be adjusted to a value in a range from about 200 to about 400 mOsm/kg, preferably in a range from about 240 to about 360 mOsm/kg or the osmolality must be close to the physiological level e.g. in the physiological range from about 290 to about 310 mOsm/kg.

2. Agents to adjust the pH of or to buffer the vaccine composition. Normally, pH of the vaccine composition is in a range of from about 5 to about 8.5. Suitable pH adjusting agents or buffer substances include hydrochloric acid, sodium hydroxide (to adjust pH) as well as phosphate buffer, Tris buffer, citrate buffer, acetate buffer, histidine buffer etc. (to buffer the vaccine).

3. Other additives like e.g. surface-active agents, antioxidants, chelating agents, antibacterial agents, viral inactivators, preservatives, dyes, anti-foaming agents, stabilizers or surface active agents, or combinations thereof.

The surface-active agent may be hydrophilic, inert and biocompatible, such as, e.g., poloxamers such as e.g. Pluronic F68 or Pluronic 127.

The antibacterial agents may be e.g. amphotericin or any derivative thereof, chlorotetracyclin, formaldehyde or formalin, gentamicin, neomycin, polymyxin B or any derivative thereof, streptomycin or any combination thereof.

The antioxidants may be e.g. ascorbic acid or tocopherol or any combination thereof.

The viral inactivators may be e.g. formalin, beta-propiolactone, UV-radiation, heating or any combination thereof.

The preservatives may be e.g. benzethonium chloride, EDTA, phenol, 2-phenoxyethanol or thimerosal or any combination thereof. EDTA has also been shown to be a chelating agent, an antioxidant and a stabilizer.

The dyes may be e.g. any indicators (such as e.g. phenol red) or brilliant green or any combination thereof.

The anti-foaming agents may be e.g. polydimethylsilozone.

The surfactants may be e.g. anionic, cationic or non-ionic or zwitterionic, such as e.g. polyoxyethylene and derivatives thereof, polysorbates (such as e.g. polysorbate 20 or polysorbate 80), Tween 80, poloxamers (such as e.g Pluronic F68) or any combination thereof.

Typically, the concentration of monoglyceride in a vaccine composition is in an amount in the range of about 0.1 g to about 5.0 g per 100 mL, or in the range of about 0.1 g about 2.0 g per 100 ml, or about 0.5 g to about 2.0 g, such as 0.5 g to about 1.5 g per 100 mL of the vaccine composition.

Furthermore, the concentration of the one or more carboxylic acids is in an amount in the range of about from 0.1 g to about 5.0 g per 100 mL, or in the range of about 0.1 g to about 2.0 g per 100 mL or about 0.5 g to about 2.0 g, such as 0.5 g to about 1.5 g per 100 mL of the vaccine composition.

The one or more monoglycerides together with one or more carboxylic acids in an vaccine composition may be in an amount of at the most 10% w/v, or at the most 5% w/v, or at the most 4% w/v, or at the most 3% w/v, or at the most 2% w/v or at the most 1% w/v or at the most 0.5% w/v or at the most 0.1% w/v or at the most 0.05% w/v.

The adjuvant may comprise a combination of lipids selected from the group consisting of mono-olein, oleic acid, lauric acid, and soybean oil. In one suitable embodiment, the adjuvant comprises oleic acid, lauric acid in Tris buffer. Suitably, this embodiment comprises 0.25 g to 0.75 g of oleic acid, 0.25 g to 0.75 g of lauric acid in 7-15 mL of Tris buffer (pH 7-9). A specific example comprises 0.4 g to 0.5 g of oleic acid, 0.3 g to 0.4 g of lauric acid in 8-10 mL of 0.1 M Tris buffer (pH 7-9). In a further suitable embodiment, the adjuvant comprises oleic acid and mono-olein in Tris buffer. Suitably, this embodiment comprises 0.25 g to 0.75 g of oleic acid, 0.25 g to 0.75 g of mono-olein in 7-15 mL of Tris buffer. A specific example comprises 0.3 g to 0.4 g of oleic acid, 0.4 g to 0.5 g of mono-olein in 8-10 mL of 0.1 M Tris buffer (pH 7-9). A further embodiment comprises 0.5 g to 0.25 g of mono-olein, 0.5 g to 0.25 g of oleic acid, and 0.25 g to 0.75 g of soybean oil in 7-15 mL of Tris buffer. A specific example of this embodiment comprises 0.1 g to 0.2 g of mono-olein, 0.8 g to 1.5 g of oleic acid, and 0.5 g to 0.6 g of soybean oil in 8-12 mL of Tris buffer (pH 7-9).

Three types of adjuvants were used successfully in the examples below: Example adjuvant A comprising 0.4 g to 0.5 g of oleic acid, 0.3 g to 0.4 g of lauric acid in 8-10 mL of 0.1 M Tris buffer (pH 7-9); Example adjuvant B comprising 0.3 g to 0.4 g of oleic acid, 0.4 g to 0.5 g of mono-olein in 8-10 mL of 0.1 M Tris buffer (pH 7-9); and Example adjuvant C comprising 0.1 g to 0.2 g of mono-olein, 0.8 g to 1.5 g of oleic acid, and 0.5 g to 0.6 g of soybean oil in 8-12 mL of Tris buffer (pH 7-9). These adjuvants are typically prepared in w/v concentration of 2-12% lipid content (6 g-12 g per 100 mL), most typically from 3-10%, such as 4%, 5%, 6%, 7, 8%, or 9%. These concentrations are those of the adjuvant mix itself. This adjuvant is then mixed with the antigen containing composition in 2:1 to 1:8 ratios, such as, for example, in a 1:1 ratio so as to provide a 4% lipid content vaccine composition when commencing from an adjuvant with an 8% lipid concentration. Typically, the lipid content in the vaccine composition of the invention is 0.5% to 6% w/v, typically as 1% to 6% w/v, more typically 1% to 4%.

The Example B composition is an Endocine™ formulation comprising equimolar amounts of glycerol monooleate and oleic acid and has been found to be exceptionally effective in naive subjects. In a highly preferred embodiment, this 8% lipid formulation is diluted with the antigen containing compositions so as to provide a vaccine composition with a lipid concentration of 1-4% w/v.

As stated, the composition is suitable for use in a method for immunization during a peri-pandemic or pandemic period comprising intranasally administering the vaccine composition of the invention. The method for immunization during a peri-pandemic or pandemic period can be used for subjects of all age. The invention further relates to a method of immunization during seasonal epidemics of paediatric subjects comprising intranasally administering a vaccine composition as described.

As stated, the invention is directed to a method of immunization of naïve subjects comprising intranasally administering a vaccine composition.

The Examples below show the efficacy of this vaccine composition in naive subjects.

The surprisingly efficacy in eliciting an immune response in naïve individuals implies that the vaccine of the invention is able to elicit immune response in individuals who have a weakened immune system in terms of being able to respond to invasive pathogens such as vira where they do not already have strong pre-existing immunity. A composition of the invention is therefore suitable for immuno-compromised individuals. Accordingly, a further aspect of the invention is directed to a vaccine composition comprising adjuvanted non-live influenza antigens intranasally administered to pediatric immune-compromised patients, including those with HIV; subjects taking immunosuppressant drugs, recent organ recipients; premature babies, and post-operative patients.

This aspect relates to a composition, said composition comprising
i) one or more non-live antigens, and
ii) an adjuvant comprising:
  one or more carboxylic acids,
  an aqueous medium, and
  optionally one or more mono-glycerides.
for use as an intranasally administered vaccine in pediatric immuno-compromised patients.

Immuno-compromised individuals have an increased susceptibility to opportunistic pathogens e.g. influenza virus and are at an increased risk for hospitalization and death from influenza. Immuno-compromised individuals and in particular pediatric immune-compromised individuals may be a suitable patient class for immunization with a composition of the present invention. On embodiment of the present invention may therefore be a composition comprising
i) one or more non-live influenza virus antigens, and
ii) an adjuvant comprising:
  one or more carboxylic acids,
  an aqueous medium, and
  optionally one or more mono-glycerides.
for use as an intranasally administered vaccine in pediatric immuno-compromised patients.

A surprising effect of the present invention as illustrated by example 2 is that the composition of the present invention is able to reduce virus shedding. Children shed more virus than immune-competent healthy adults, which leads to increased virus spreading to other people in their proximity. The present invention may therefore be suitable for treating paediatric populations such as infants, children and adolescents. The present invention may be suitable for preventing virus spreading by a pediatric population. In one embodiment the composition of the present invention is for use in pediatric subjects such as infants, children and the adolescents. In one embodiment the composition of the present invention is for use in naive subjects for reducing virus shedding. In one embodiment the composition of the present invention in for use in influenza naive subjects for reducing virus shedding. Further, a composition of the present invention may be particularly suitable for containing a pandemic by reducing virus spreading. In one embodiment a composition of the present invention is for use in naive subjects for reducing virus shedding in a pandemic zone. In one embodiment a composition of the present invention is for use in naive subjects for reducing virus shedding during a peri-pandemic period. In one embodiment a composition of the present invention is for use in the pediatric subjects for reducing virus shedding during a pen-pandemic period.

A method of immunization against influenza in pediatric immuno-compromised patients by intranasal administration of a composition as described supra is an interesting aspect of the surprising result.

The composition is typically for use as an intranasally administered vaccine to pediatric immuno-compromised subjects against influenza. The pediatric immune-compromised subjects are suitably selected from the group consisting of people who are HIV infected; subjects taking immunosuppressant drugs, such as recent organ recipients; premature babies, and post-operative patients.

A further aspect of the invention is directed to a vaccine for use in naive subjects and pediatric immuno-compromised patients. The adjuvant of the invention has demonstrated its efficacy in influenza naive subjects. This renders it suitable for both naive patient classes and pediatric immune-compromised patients.

Accordingly, a further aspect of the invention is directed to a composition for use as an intranasally administered vaccine for use in naive subjects and pediatric immuno-compromised patients, said composition comprising
i) one or more non-live antigens, and
ii) an adjuvant comprising:
  one or more carboxylic acids,
  an aqueous medium, and
  optionally one or more mono-glycerides.

Suitable types of vaccines for immunization of naive subjects and pediatric immuno-compromised patients comprise, according to the present invention, an antigen of the respectively relevant pathogen intended to be immunized or treated by vaccine This includes, without being limited to, immunogens derived from viruses selected from the group consisting of hepatitis B, hepatitis A, hepatitis C, hepatitis D & E virus, Non-A/Non-B Hepatitis virus, pox and smallpox viruses, polio virus, measles virus, human immunodeficiency virus (HIV), enteroviruses, retroviruses, respiratory syncytial virus, rotavirus, human papilloma virus, varicella-zoster virus, yellow fever virus, SARS virus, animal viruses, herpes viruses, cytomegalovirus, varicella zoster, Epstein Barr virus, para-influenza viruses, adenoviruses, coxsakie viruses, picorna viruses, rhinoviruses, rubella virus, papo-virus, and mumps virus. Some non-limiting examples of known viral antigens other than the Influenza virus antigens mentioned above may include the following: antigens derived from HIV-I such as tat, nef, gpI20 or gpI[beta]O, gp40, p24, gag, env, vif, vpr, vpu, rev or part and/or combinations thereof; antigens derived from human herpes viruses such as gH, gL gM gB gC gK gE or gD or or part and/or combinations thereof or Immediate Early protein such as ICP27, ICP47, ICP4, ICP36 from HSVI or HSV2; antigens derived from cytomegalovirus, especially human cytomegalovirus such as gB or derivatives thereof; antigens derived from Epstein Barr virus such as gp350 or derivatives thereof; antigens derived from Varicella Zoster Virus such as gp I, 11, 111 and IE63; antigens derived from a hepatitis virus such as hepatitis B, hepatitis C or hepatitis E virus antigen (e.g. env protein EI or E2, core protein, NS2, NS3, NS4a, NS4b, NS5a, NS5b, p7, or part and/or combinations thereof of HCV); antigens derived from human papilloma viruses (for example HPV6, 11, 16, 18, e.g. LI, L2, EI, E2, E3, E4, E5, E6, E7, or part and/or combinations thereof); antigens derived from other viral pathogens, such as Respiratory Syncytial virus (e.g F and G proteins or derivatives thereof), parainfluenza virus, measles virus, mumps virus, flaviviruses (e.g. Yellow Fever Virus, Dengue Virus, Tickborne encephalitis virus, Japanese Encephalitis Virus) or part and/or combinations thereof.

The composition of the invention may comprise non-live antigens of the following viruses but are not limited to: non-live antigens from Herpes zoster, HIB, Pertussis, Polio, Tetanus, Diphteria, Hepatitis A, Seasonal Influenza, Influenza A, Influenza B, Respiratory syncytial virus (RSV), Human metapneumovirus (hMPV), Human papillomavirus (HPV), Rotavirus, Norovirus, Human immunodeficiency virus (HIV), Herpes simplex, and/or Parainfluenza virus (OIV), Rhino virus, Severe acute respiratory syndrome (SARS), Coronaviruses, Herpes zoster/varicella, Hepatitis A-E, Hantavirus, and/or Cytomegalovirus, or mixtures thereof, The compostion of the invention may comprise non-live antigens of the following bacteria but are not limited to: non-live antigens from *Pneumococci, Meningococci, Haemophilus influenzae* b, (Hib) *Bacillus anthracis, Chlamydia trachomatis, Pseudomonas aeruginosa, Mycobacterium tuberculosis, Diphtheria, Escherichia coli.* Group *Streptococcus, Neisseria gonorrhoeae, Bordetella pertussis* or mixtures thereof, The antigens may be e.g. whole non-live antigens such as e.g. whole inactivated viruses. The antigen may also be part of a pathogen such as e.g. part of an inactivated virus. The antigen components that may be used are, but not limited to, for example, viral, bacterial, mycobaterial or parasitic antigens. Bacterial pathogens may be e.g. Mycobacteria causing tuberculosis and leprosy, pneumocci, aerobic gram negative or gram-positive bacilli, *mycoplasma*, staphylococcal infections, streptococcal infections, *Helicobacter pylori*, salmonellae, *Bordetella pertussis* and chlamydiae. The diseases may also be bacterial infections such as infections caused by Mycobacteria causing tuberculosis and leprosy, pneumocci, aerobic gram negative bacilli, *mycoplasma*, staphyloccocal infections, streptococcal infections, *Helicobacter pylori*, salmonellae, *diphtheria, Bordetella pertussis* causing whooping cough, and chlamydiae.

Preferred types of vaccines for immunization of naive subjects and immune-compromised patients may be selected from the group consisting of pneumococcal vaccine, Hepatitis A-E vaccine, *Meningococci* vaccine, *Haemophilus influenzae* b (Hib) vaccine, *Diphtheria* vaccine and DTaP vaccine (protects from *diphtheria*, tetanus, and pertussis (whooping cough)).

The diseases may also be parasitic such as, e.g. malaria, leishmaniasis, trypanosomiasis, toxoplasmosis, schistosomiasis, filariasis or various types of cancer such as, e.g. breast cancer, stomach cancer, colon cancer, rectal cancer, cancer of the head and neck, renal cancer, malignant melanoma, laryngeal cancer, ovarian cancer, cervical cancer, prostate cancer.

The diseases may also be allergies due to house dust mite, pollen and other environmental allergens and autoimmune diseases such as, e.g. systemic lupus erythematosis.

The antigen in the vaccine composition may be whole non-live antigens such as e.g. whole inactivated viruses, split non-live antigens or subunit non-live antigens. Inactivation processes are well known in the art such as heat inactivation, irradiation inactivation by UV-light or in activation by formalin inactivation or treatment with beta-propiolactone.

The composition of the invention are for use as vaccines for immunization of naive subjects and pediatric immunocompromised patients. The pediatric immune-compromised patients are suitably selected from the group consisting of people who are HIV infected subjects; subjects taking immunosuppressant drugs, such as recent organ recipients; premature babies, and post-operative patients. The naive subjects may be children under 18 years old, such as children 0 to 18 years, particularly children aged 12 and under. Typically, the children are less than 8 years of age, such as 6 years old or less. An important intended class of patients for the vaccine of the invention is particularly children of 2 months to less than 9 years of age, typically children of age 3 months to less than 9 years old, such as of age 6 months to less than 8 years old, most typically of age 6 month to less than 7 years old, such as of age 6 months to less than 72 months, or of age 6 months to 60 months or of age 6 months to 24 months. The composition of the invention is intended, at least in part, as a vaccine for pediatric use.

The naive subjects may be of all age groups when the composition is particularly directed to a vaccine for use during pandemic or peri-pandemic period.

*Streptococcus pneumoniae* is a major cause of morbidity and mortality worldwide with an estimated 1.6 million people dying of invasive pneumococcal disease (IPD) each year (WHO, 2002). IPD occurs most commonly among the very young (<24 months) and the elderly (>65 years); the elderly have the highest IPD mortality rates. Currently, four vaccines are available for the prevention of infection with *Streptococcus pneumoniae*. No intranasal vaccines are available for *Streptococcus pneumonia*.

One interesting embodiment of the invention is directed to an intranasal alternative for the prevention of infection with *Streptococcus pneumoniae*, directed particularly at infants, children, adolescents and other *Streptococcus pneumoniae* naive subjects. The composition of the invention does not utilize live attenuated bacteria but rather non-live *Streptococcus pneumonia* antigens. The surprisingly efficacy of the vaccine of the invention is a result of the adjuvant used and the surprising result was specific for naive subjects. Similar results are anticipated also for immuno-compromised subjects.

Accordingly, a further aspect of the invention is directed to a composition for use as an non-live intranasally administered vaccine for use in naive subjects and pediatric immune-compromised patients for the prevention of infection with *Streptococcus pneumoniae* or for reducing the severity of symptoms associated with an with *Streptococcus pneumonia* infection, said composition comprising
i) one or more *Streptococcus pneumoniae* antigens, and
ii) an adjuvant comprising:
one or more carboxylic acids,
an aqueous medium, and
optionally one or more mono-glycerides.

The immuno-compromised patients are suitably selected from the group consisting of infants, children and adolescent who are; HIV infected subjects; subjects taking immuno-suppressant drugs, such as recent organ recipients; premature babies, and post-operative patients An important embodiment of the invention is directed to a vaccine against pneumococcal infection for the prevention of and/or reducing of the symptoms of disease states selected from the group consisting of bronchitis, pneumonia, septicemia, pericarditis, meningitis and peritonitis.

One embodiment is related to the use of pneumococcal vaccine, such as a pneumococcal polysaccharide vaccine (PPV) in pediatric subjects, particular for use in subjects from 4 weeks of age to 6 years of age (e.g. to subjects that are immunologically naïve to pneumococcal antigens and with immune systems not fully developed).

The vaccine composition according to the invention may further comprise pharmaceutically acceptable excipients such as e.g. a medium which may be an aqueous medium further comprising a surface-active agent, which may be hydrophilic and inert and biocompatible, such as, e.g., poloxamers such as e.g. Pluronic F68 or Pluronic 127.

A pneumococcal vaccine according to present invention may further comprise antibacterial agents, antioxidants, viral inactivators, preservatives, dyes, stabilizers, anti-foaming agents, surfactants (non-ionic, anionic or cationic) as described herein, or any combination thereof. The antibacterial agents may be e.g. amphotericin or any derivative thereof, chlorotetracyclin, formaldehyde or formalin, gentamicin, neomycin, polymyxin B or any derivative thereof, streptomycin or any combination thereof. The antioxidants may be e.g. ascorbic acid or tocopherol or any combination thereof. The pathogenic e.g. viral and/or bacterial inactivators may be e.g. formalin, beta-propiolactone, UV-radiation, heating or any combination thereof.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

EXAMPLES

Example 1

Objective

The objective of the present study was to investigate the immunogenicity and protective efficacy of intranasally administered adjuvant-formulated influenza split antigen and adjuvant-formulated killed whole influenza virus antigen in the ferret model, according to the present invention.

The vaccine based on H1N1/California/2009 split antigen (vaccine A) was studied with antigen doses of 5, 15, or 30 µg HA and the vaccine based on H1N1/California/2009 killed whole virus antigen (vaccine B) was studied with an antigen dose of 15 µg HA. Vaccine efficacy was studied using wild-type H1N1 A/The Netherlands/602/2009 virus as challenge.

The Endocine™ adjuvant comprised equimolar amounts of glycerol monooleate and oleic acid with a final concentration of 20 mg/ml (2%) in the vaccine composition. In this experiment Immunose™ FLU means non-live influenza antigens mixed with Endocine™.

Experimental Groups Immunization Phase

TABLE 1

| Group number | Number of animals | Test substance | Antigen dose (µg HA) | Route of immunization |
|---|---|---|---|---|
| 1 | 6 | Saline | 0 | Nasal |
| 2 | 6 | Fluarix ® | 15 per strain | Subcutaneous |
| 3 | 6 | Vaccine A | 5 | Nasal |
| 4 | 6 | Vaccine A | 15 | Nasal |
| 5 | 6 | Vaccine A | 30 | Nasal |
| 6 | 6 | Vaccine B | 15 | Nasal |

Vaccine Preparation and Administration

Saline: 0.9% saline pH 5-5.5.

Fluarix®: Parenteral vaccine (composed of A/California/7/2009 (H1N1)-like, A/Perth/16/2009 (H3N2)-like and B/Brisbane/60/2008-like vaccine strains at 15 µg HA of each vaccine strain in 0.5 ml). Animals of group 2 were vaccinated subcutaneously at day 21 and 42 with 0.5 ml Fluarix (GlaxoSmithKline Biologicals). Vaccine A: Influenza vaccine nasal drops, 5, 15 and 30 µg HA/0.2 ml, adjuvant formulation comprising an Endocine™ formulation of equimolar amounts of glycerol monooleate and oleic acid (pH 8, in Tris 0.1 M) with a final concentration of 20 mg/ml in the vaccine compositional: H1N1/California/2009 split antigen.

Vaccine B: Influenza vaccine nasal drops, 15 µg HA/0.2 ml, adjuvant formulation comprising an Endocine™ formulation of equimolar amounts of glycerol monooleate and oleic acid (pH 8, in Tris 0.1M) with a final concentration of 20 mg/ml in the vaccine composition, H1N1/California/2009 killed whole virus antigen.

Ferrets

Healthy female ferrets (*Mustela putorius* furo: outbred), approximately 12 months of age, with body weights of 760-1210 g and seronegative for antibodies against circulating influenza viruses B, A/H1N1, A/H3N2 and A/pH1N1 as demonstrated by hemagglutination inhibition (HI) assay were used. Animals were housed in normal cages, in groups of maximal 8 animals during the pre-immunization phase and in study groups of 6 animals during the immunization phase. The study groups were transferred to negatively pressurized glovebox isolator cages on the day of challenge. During the whole study animals were provided with commercial food pellets and water ad libitum.

Immunization

Five groups of six ferrets received three intranasal immunizations (droplets: 100 µl in each nostril, using a pipet with filtertip) under anesthesia with ketamine and domitor at days 0, 21 and 42. Animals of group 1 received 200 µl of steril physiological saline (0.9% saline pH5-5.5). Groups 3, 4 and 5 were intranasally immunized with 200 µl Endocine™ formulated H1N1/California/2009 split antigen containing 5, 15 and 30 µg HA, respectively. Group 6 was intranasally immunized with 200 µl Endocine™ formulated H1N1/California/2009 whole virus antigen containing 15 µg HA. Control group 1 received 200 µl of saline intranasally. One group of six ferrets (group 2) were vaccinated subcutaneously at day 21 and 42 with 0.5 ml Fluarix® (GlaxoSmithKline Biologicals), season 2010/2011, a non-adjuvanted trivalent influenza vaccine (TIV) that contained 15 µg HA of each vaccine strain. Blood samples for serum preparation were collected prior immunization on days 0, 21 and 42 and before challenge on study days 64 and 70.

Challenge Virus Preparation and Administration

On study day 70, all animals were challenged with a field isolate of influenza virus (H1N1 strain A/The Netherlands/602/2009) by the intratracheal route. To prepare the challenge virus, the H1N1 A/The Netherlands/602/2009 challenge stock (7.8 log 10 TCID50/ml) was diluted in ice-cold PBS to a concentration of $3.3 \times 10^5$ TCID50/ml. All animals were challenged intratracheally with 3 ml of the challenge virus preparation containing $10^6$ TCID50, administered with a small catheter into the trachea using a tracheoscope and released just above the bifurcation. Preparation and administration of the challenge virus were performed under BSL3 conditions. One day after challenge a sample of the remaining challenge virus dilution was titrated on Madin-Darby canine kidney (MDCK) cells to confirm the infectivity of the virus. Back titration of the challenge dilution one day after the inoculation showed that the material still contained 4.8 log 10 TCID50.

Procedures and Sample Collection

Several procedures were performed on the ferrets over the course of the experiment. For implantation of temperature sensors, immunizations, viral challenge and computed tomography (CT) imaging the animals were anesthetized with a cocktail of ketamine (4-8 mg/kg: i.m.; Alfasan, Woerden, The Netherlands) and domitor (0.1 mg/kg: i.m.; Orion Pharma, Espoo, Finland). For sampling (blood, swabs and nasal washes) and euthanasia by exsanguination, the animals were anesthetized with ketamin. Two weeks prior to the start of the experiment, a temperature logger (DST micro-T ultrasmall temperature logger; Star-Oddi, Reykjavik, Iceland) was placed in the peritoneal cavity of the ferrets. This device recorded body temperature of the animals every 10 minutes. Ferrets were weighed prior to each immunization (days 0, 21 and 42) and on the days of challenge and euthanasia (days 70 and 74). Animals of groups 1, 2 and 4 were monitored by CT imaging on days 64, 71, 72, 73 and 74. Blood samples were collected prior to the immunization on days 0, 21 and 42, on day 64 and before challenge on day 70. Nose and throat swabs were collected prior challenge on day 70 and on each day after challenge.

Collection of Blood Samples and Serum

Blood samples were collected and split in 2 equal volumes. One volume, used to isolate PBMC, was immediately transferred to a tube containing EDTA anti-coagulant. The other volume, used to collect serum, was transferred to a serum tube containing clot activator. All serum tubes were centrifuged at ca. $2000 \times g$ for 10 minutes at room temperature. Serum was aliquoted in 0.1 ml samples and stored at ca. $-80°$ C.

Isolation of PBMC and Plasma

Blood samples, used to isolate PBMC, were immediately transferred to a tube containing EDTA anti-coagulant, centrifuged at $880 \times G$ for 5 min, the plasma was stored at ca. $-80°$ C. The cell pellet was resuspended in 3.5 ml wash buffer (D-PBS: lot #: RNBB7791, V-CMS: 10700395 and EDTA: lot #: 079K8712, V-CMS: 10700037), layered on 3 ml lymphoprep and centrifuged at $800 \times G$ for 30 minutes. After centrifugation the cell containing interface was collected, transferred to a new tube and 4 times washed in wash buffer. Centrifugation at $600 \times g$, $465 \times g$ and $350 \times g$ for 10 min and at $250 \times g$ for 15 min was involved in the subsequent washing steps. After the last wash step, the cell pellet was resuspended, put on ice for at least 10 min, resuspended in 1 ml ice cold freeze medium (RPMI lot #1MB078, 20% FCS VC #201110194, 10% DMSO VC #10700203), transferred to an ampoule, and stored at $-80°$ C.

Serology

Antibody titers against H1N1 A/The Netherlands/602/2009 and 2 distant viruses H1N1 A/Swine/Ned/25/80 and H1N1 A/Swine/Italy/14432/76 were determined by hemagglutination inhibition assay (HI) and virus neutralization assay (VN). Antibody titers against the distant virus H1N1 A/New Jersey/08/76 were determined by hemagglutination inhibition assay.

HI Assay

The HI assay is a standard binding assay based on the ability of influenza virus hemagglutinin specific antibodies to block influenza induced agglutination of red blood cells. The samples were pre-treated with cholera filtrate (obtained from *Vibrio cholerae* cultures) in order to remove non-specific anti-hemagglutinin activity. Following an incubation for 16 hours at 37° C. the cholera filtrate was inactivated by incubating the samples for 1 hour at 56° C. Serial two-fold dilutions of the samples were made in phosphate buffered sulphate (PBS) (in duplicate 96-wells plates starting with a dilution of 1:20) and when the samples showed a-specific hemagglutination, they were pre-treated with turkey erythrocytes. After removal of these erythrocytes the samples were incubated with a fixed concentration of 4 hemagglutination units (HAU) of the concerning influenza virus for 1 hour at 4° C. Finally, the plates were scored independently for inhibition of hemagglutination, as shown by sedimentation of the erythrocytes. Trending ferret control sera were included in all runs.

VN Assay

The VN assay is a standard assay based on the ability of a subset of influenza virus-specific antibodies to neutralize the virus such that there will be no virus replication in the cell culture. The samples were heat-inactivated for 30 minutes at 56° C. and subsequently serial two-fold dilutions of the samples were made in infection medium (Eagles minimal essential medium supplemented with 20 mM Hepes, 0.075% sodium bicarbonate, 2 mM L-Glutamine, 100 IU/ml of penicillin and streptomycin, 17.5 µg/ml trypsin and 2.3 ng/ml amphotericin B) in triplicate in 96-wells plates starting with a dilution of 1:8. The sample dilutions were then incubated with 25-400 TCID50 of the concerning virus for 1 hour at 37° C., 5% CO2. After completion of the 1 hour incubation period the virus-antibody mixtures were transferred to plates with Madine Darby Canine Kidney (MDCK) cell culture monolayers that were 95-100% confluent. These plates were than incubated for 1 hour at 37° C., 5% CO2, and the virus-antibody mixtures were subsequently removed and replaced by infection medium. After an incubation period of 6 days at 37° C., 5% CO2 the plates were read using turkey erythrocytes to detect the presence of influenza virus hemagglutinin. The VN titers were calculated according to the method described by Reed and Muench (Reed, L. J.; Muench, H. (1938). "A simple method of estimating fifty percent endpoints". The American Journal of Hygiene 27: 493-497).

Virus Replication in the Upper and Lower Respiratory Tract

On days 0, 1, 2, 3 and 4 after challenge, nose and throat swabs were taken from the animals under anesthesia. Four days after challenge, the ferrets were euthanized by exsanguination under anesthesia after which full-body gross-pathology was performed and tissues were collected.

Samples of the right nose turbinate and of all lobes of the right lung and the accessory lobe were collected and stored at −80° C. until further processing. Turbinate and lung samples were weighed and subsequently homogenized with a FastPrep-24 (MP Biomedicals, Eindhoven, The Netherlands) in Hank's balanced salt solution containing 0.5% lactalbumin, 10% glycerol, 200 U/ml penicillin, 200 µg/ml streptomycin, 100 U/ml polymyxin B sulfate, 250 µg/ml gentamycin, and 50 U/ml nystatin (ICN Pharmaceuticals, Zoetermeer, The Netherlands) and centrifuged briefly before dilution.

After collection, nose and throat swabs were stored at −80° C. in the same medium as used for the processing of the tissue samples. Quadruplicate 10-fold serial dilutions of lung and swab supernatants were used to determine the virus titers in confluent layers of MDCK cells as described previously (Rimmelzwaan G F et al., J Virol Methods 1998 September; 74(1)57-66).

Antibody Titer Results

Serum levels of antibodies were determined on days 0, 21, 42, 64, and 70 prior to each immunization. Titers against H1N1 A/The Netherlands/602/2009 and 2 distant viruses (H1N1 A/Swine/Ned/25/80 and H1N1 A/Swine/Italy/14432/76 were determined by hemagglutination inhibition assay (HI) and virus neutralization assay (VNT). Antibody titers against the distant virus H1N1 A/New Jersey/08/76 were determined by hemagglutination inhibition assay (HI).

HI antibody titers—Homologous: H1N1 A/The Netherlands/602/2009

The geometric mean HI titers are depicted in FIG. 1. The ≤5 value was replaced with the corresponding absolute value 5 for calculation of the geometric mean. All pre-sera (day 0) were HI antibody negative (titer: ≤5).

Analysis of the HI titers by group revealed the following results:

Group 1 (Saline; Infection Control)

All serum samples were HI antibody negative.

Group 2 (Fluarix®; Parenteral Control)

One serum sample collected after the first immunization (day 42) was low HI antibody positive (titer: 13). Low HI titers (range 13-70) were detected after the second immunization in sera of five out of six animals.

Group 3 (Vaccine A, 5 µg HA; Intranasal)

All samples collected after the first immunization were HI antibody positive (day 21; GMT: 477, range 160-1120). HI antibody titers increased considerably after the second immunization (day 42; GMT: 1669, range 1120-2560) and in four out of six animals also after the third immunization (day 64; GMT: 2158, range 1280-3840). Samples collected on day 70 (day of challenge) showed HI titers comparable to those measured at day 64 (day 70; GMT: 2103, range 1120-3840).

Group 4 (Vaccine A, 15 µg HA; Intranasal)

Five out of six samples collected after the first immunization were HI antibody positive (day 21; GMT: 1130 range, 5-5760). All samples collected after the second immunization were HI antibody positive; HI antibody titers increased considerably in five animals (day 42; GMT: 3673, range, 1120-5760). The third immunization did not result in increased HI antibody titers (day 64; GMT: 2386, range 1920-4480). Samples collected on day 70 (day of challenge) showed HI titers comparable to those measured at day 64 (day 70; GMT: 2281, range 1280-2560).

Group 5 (Vaccine A, 30 µg HA; Intranasal)

All samples collected after the first immunization were HI antibody positive (day 21; GMT: 1249, range 400-3200). HI antibody titers increased in five out of six animals after the second immunization (day 42; GMT: 1874, range 640-3840) and in two animals also after the third immunization (day 64; GMT: 1837 range 1280-3200). Samples collected on day 70 (day of challenge) showed HI titers comparable to those measured at day 64 (day 70; GMT: 1699, range 640-3200).

Group 6 (Vaccine B, 15 µg HA; Intranasal)

Five out of six samples collected after the first immunization were HI antibody positive (day 21; GMT: 87, range 5-1280). HI antibody titers increased considerably in all animals after the second immunization (day 42; GMT: 577, range 100-2880) and in two animals also after the third immunization (day 64; GMT: 626, range 160-2560). Samples collected on day 70 (day of challenge) showed HI titers comparable to those measured at day 64 (day 70; GMT: 583, range 160-2240).

Heterologous: H1N1 A/Swine/Ned/25/80, H1N1 A/Swine/Italy/14432/76 and H1N1 A/New Jersey/08/76

Figure 2A:
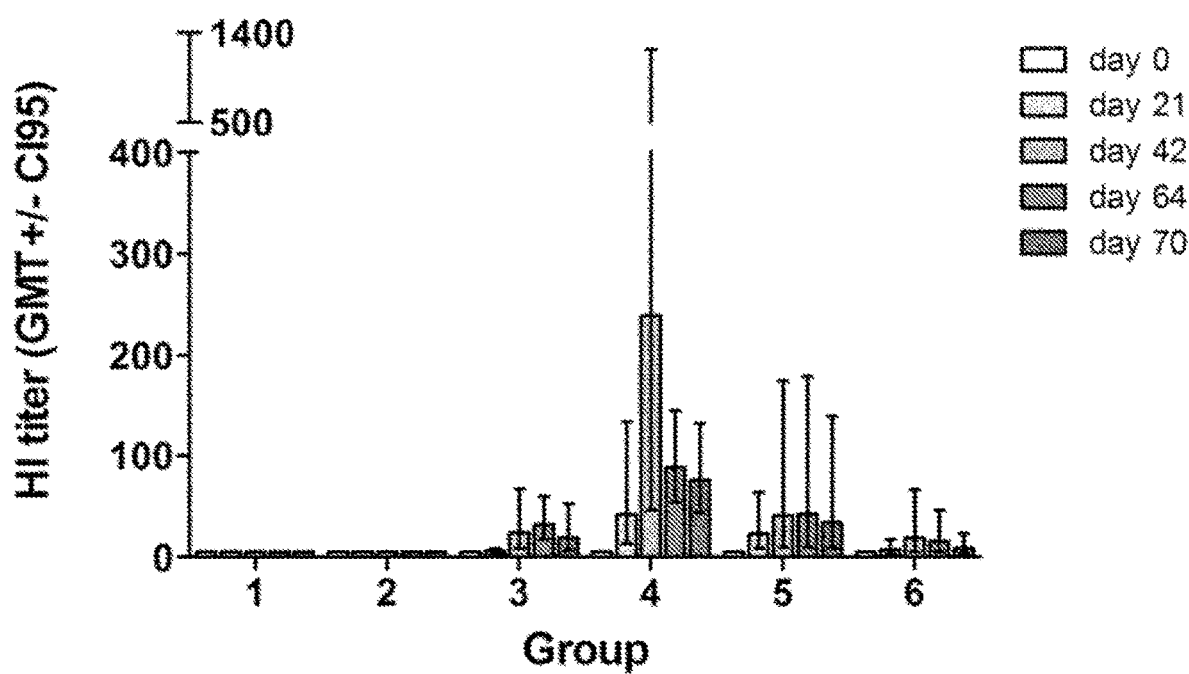
FIGS. 2A-C: HI titers against distant viruses.
Figure 2B:
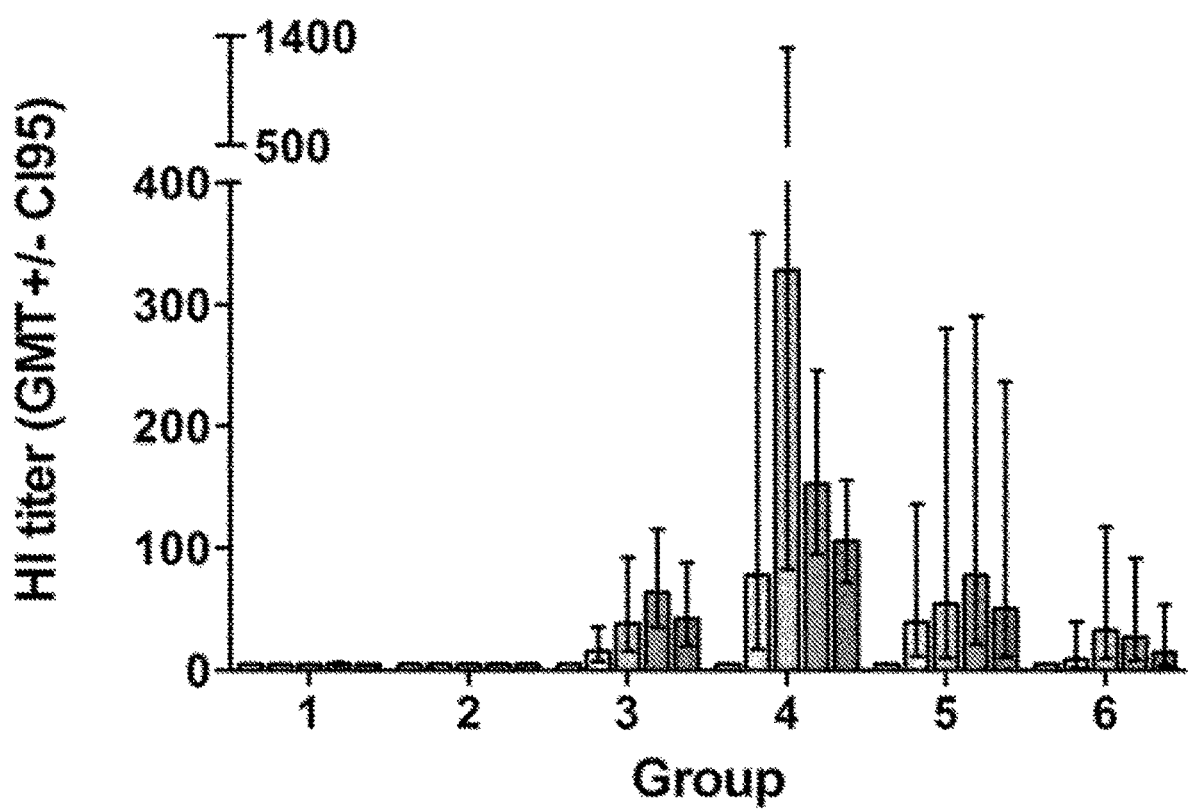
Figure 2C:
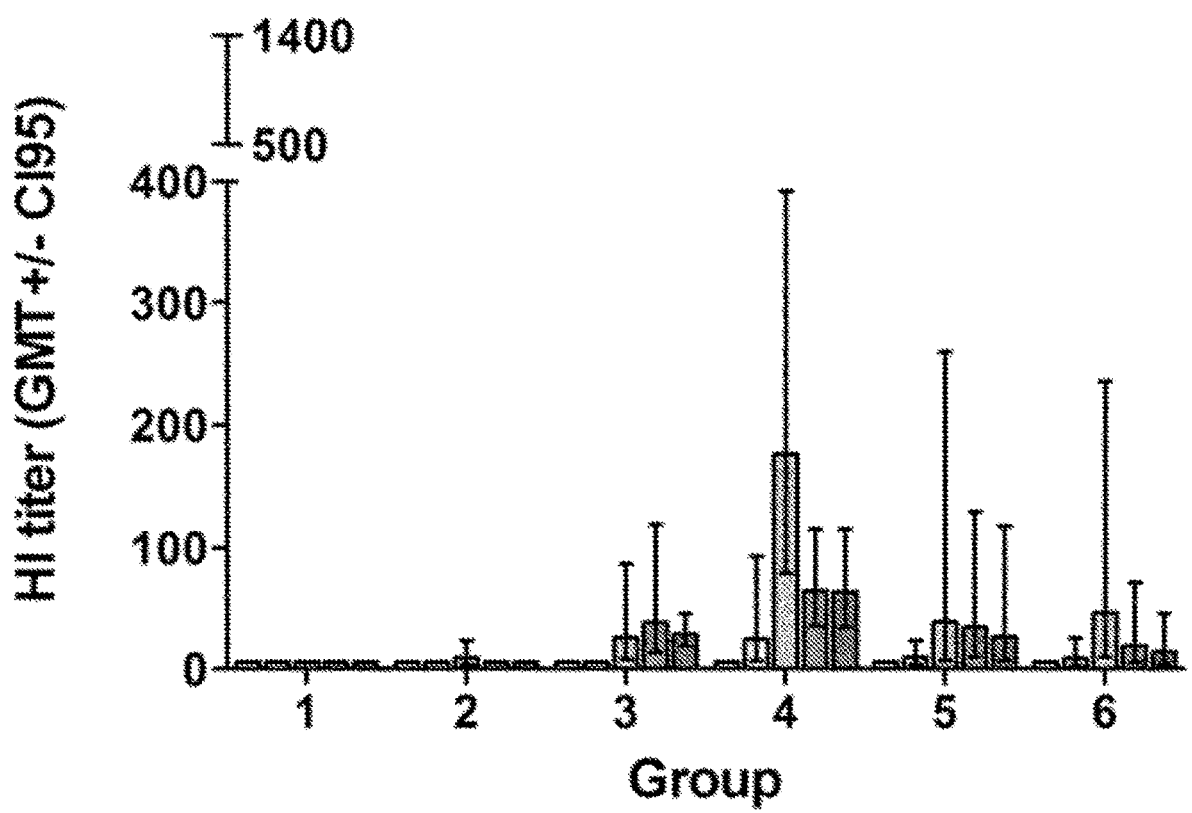

HI antibody titers against the distant viruses H1N1 A/Swine/Ned/25/80, H1N1 A/Swine/Italy/14432/76 and H1N1 A/New Jersey/08/76 were detected. The geometric mean HI titers against the distant viruses are depicted in FIG. 2. The ≤5 value was replaced with the corresponding absolute value 5 for calculation of the geometric mean. All pre-sera (day 0) were HI antibody negative (titer: ≤5). Cross-reactive HI antibody titers were considerably lower than homologous H1N1 A/The Netherlands/602/2009 HI antibody titers.

Analysis of the HI titers by group revealed the following results:

Group 1 (Saline; Infection Control)

All serum samples were HI antibody negative, except one. One sample collected on day 64 showed a very low HI antibody titer of 7.5 against H1N1 A/Swine/Italy/14432/76.

Group 2 (Fluarix®; Parenteral Control)

All samples were H1N1 A/Swine/Ned/25/80 and H1N1 A/Swine/Italy/14432/76 HI antibody negative. Low HI titers against H1N1 A/New Jersey/08/76 were detected in three out of six animals after the first immunization in sera collected on days 42.

Group 3 (Vaccine A, 5 µg HA; Intranasal)

All animals developed cross-reactive HI antibodies against the three distant viruses. The highest titers were measured after the second and/or third immunization. H1N1 A/Swine/Ned/25/80 HI antibody titers (GMT) on days 21, 42, 64 and 70 were 6 (range 5-7.5), 24 (range 5-60), 32 (range 20-80) and 19 (range 5-70), respectively. H1N1 A/Swine/Italy/14432/76 HI antibody titers (GMT) on days 21, 42, 64 and 70 were 16 (range 5-50), 38 (range 10-80), 63 (range 40-160) and 42 (range 20-120), respectively. H1N1 A/New Jersey/08/76 HI antibody titers (GMT) on days 21, 42, 64 and 70 were 5, 26 (range 7.5-70), 39 (range 5-80) and 29 (range 20-50), respectively.

Group 4 (Vaccine A, 15 µg HA; Intranasal)

All animals developed cross-reactive HI antibodies against the three distant viruses after the second immunization. The third immunization did not result in increased HI titers. H1N1 A/Swine/Ned/25/80 HI antibody titers (GMT) on days 21, 42, 64 and 70 were 42 (range 5-90), 239 (range 20-1120), 88 (range 50-160) and 75 (range 40-160), respectively. H1N1 A/Swine/Italy/14432/76 HI antibody titers (GMT) on days 21, 42, 64 and 70 were 78 (range 5-280), 327 (range 35-1280), 153 (range 80-320) and 105 (range 70-160), respectively. H1N1 A/New Jersey/08/76 HI antibody titers (GMT) on days 21, 42, 64 and 70 were 25 (range 5-80), 176 (range 60-400), 64 (range 40-140) and 63 (range 40-160), respectively.

Group 5 (Vaccine A, 30 μg HA; Intranasal)

All animals except one developed cross-reactive HI antibodies against H1N1 A/Swine/Ned/25/80. All animals developed cross-reactive HI antibodies against H1N1 A/Swine/Italy/14432/76 and H1N1 A/New Jersey/08/76. The highest titers were measured after the second and/or third immunization. H1N1 A/Swine/Ned/25/80 HI antibody titers (GMT) on days 21, 42, 64 and 70 were 23 (range 5-80), 41 (range 5-320), 42 (range 5-320) and 34 (range 5-320), respectively. H1N1 A/Swine/Italy/14432/76 HI antibody titers (GMT) on days 21, 42, 64 and 70 were 39 (range 5-160), 54 (range 5-640), 78 (range 20-720) 50 (range 5-480), respectively. H1N1 A/New Jersey/08/76 HI antibody titers (GMT) on days 21, 42, 64 and 70 were 9 (range 5-30), 40 (range 5-400), 35 (range 5-160) and 27 (range 5-160), respectively.

Group 6 (Vaccine B, 15 μg HA; Intranasal)

All animals developed cross-reactive HI antibodies against H1N1 A/Swine/Italy/14432/76. All animals except one developed cross-reactive HI antibodies against H1N1 A/Swine/Ned/25/80 and all animals except one developed cross-reactive HI antibodies against H1N1 A/New Jersey/08/76. The highest titers were measured after the second and/or third immunization. H1N1 A/Swine/Ned/25/80 HI antibody titers (GMT) on days 21, 42, 64 and 70 were 7 (range 5-40), 19 (range 5-80), 15 (range 5-80) and 9 (range 5-40), respectively. H1N1 A/Swine/Italy/14432/76 HI antibody titers (GMT) on days 21, 42, 64 and 70 were 9 (range 5-160), 32 (range 5-160), 27 (range 5-160), 15 (range 5-80), respectively. H1N1 A/New Jersey/08/76 HI antibody titers (GMT) on days 21, 42, 64 and 70 were 8 (range 5-80), 47 (range 10-240), 19 (range 5-140) and 13 (range 5-80), respectively.

VN Antibody Titers:

Homologous: H1N1 A/The Netherlands/602/2009

Figure 3:
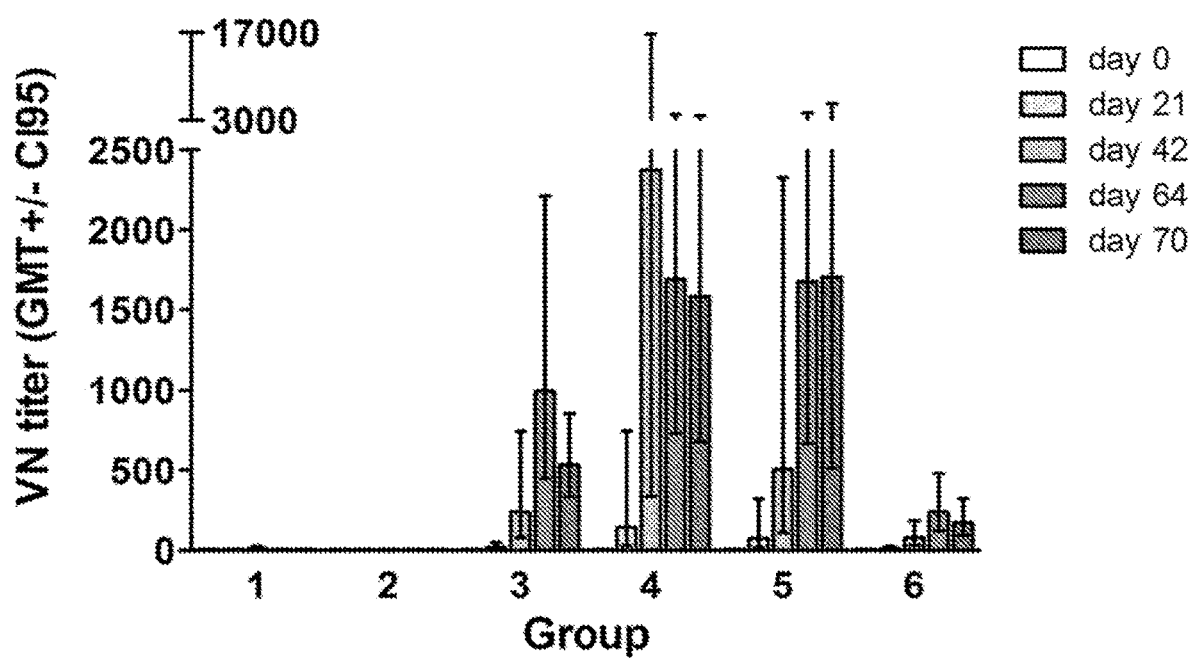
FIG. 3: Development of VN antibody titers against H1N1 A/Ned/602/09.

VN antibody titers were measured in serum samples from all experimental animals. The geometric mean VN titers are depicted in FIG. 3. All pre-sera (day 0) were VN antibody negative (titer: ≤8).

Analysis of the VN titers by group revealed the following results:

Group 1 (Saline; Infection Control)

All serum samples were VN antibody negative, except one collected on day 42 that measured ≤64.

Group 2 (Fluarix®; Parenteral Control)

All serum samples were VN antibody negative.

Group 3 (Vaccine A, 5 μg HA; Intranasal)

Four out of six samples collected after the first immunization were low VN antibody positive (day 21; GMT: 19 range, 8-64). All samples collected after the second immunization were VN antibody positive. VN antibody titers increased considerably in five animals after the second immunization (day 42; GMT: 242, range, 64-859) and after the third immunization (day 64; GMT: 995, range 362-2436). Samples collected on day 70 (day of challenge) showed comparable, or lower VN titers than those measured at day 64 (day 70; GMT: 535, range 304-859).

Group 4 (Vaccine A, 15 μg HA; Intranasal)

Five out of six samples collected after the first immunization were VN antibody positive (day 21; GMT: 147 range, 8-724). All samples collected after the second immunization were VN antibody positive. VN antibody titers increased considerably in five animals after the second immunization (day 42; GMT: 2376, range, 64-8192) and in two animals after the third immunization (day 64; GMT: 1688, range 662-4871). Samples collected on day 70 (day of challenge) showed VN titers comparable to those measured at day 64 (day 70; GMT: 1581, range 351-3444).

Group 5 (Vaccine A, 30 μg HA; Intranasal)

All samples collected after the first immunization were VN antibody positive (day 21; GMT: 74, range 11-627). VN antibody titers increased considerably in five out of six animals after the second immunization (day 42; GMT: 504, range 41-3435) and in three out of six animals after the third immunization (day 64; GMT: 1673 range 724-4884). Samples collected on day 70 (day of challenge) showed VN titers comparable to those measured at day 64 (day 70; GMT: 1699, range 304-5793).

Group 6 (Vaccine B, 15 μg HA; Intranasal)

Two out of six samples collected after the first immunization were low VN antibody positive (day 21; GMT: 12, range 8-64). All samples collected after the second immunization were VN antibody positive (day 42; GMT: 78, range 32-304). VN antibody titers increased after the third immunization (day 64; GMT: 242, range 113-747). Samples collected on day 70 (day of challenge) showed comparable, or lower VN titers than those measured at day 64 (day 70; GMT: 177, range 91-362).

Heterologous: H1N1 A/Swine/Ned/25/80, H1N1 A/Swine/Italy/14432/76. VN antibody titers against the distant viruses H1N1 A/Swine/Ned/25/80 and H1N1 A/Swine/Italy/14432/76 were tested (data not shown). All groups 3, 4, 5, and 6 outperformed groups 1 and 2 on days 42, 64 and 70.

Example 2

For all experimental animals certain clinical and pathological parameters were determined, i.e. mortality, body temperature, body weight, aerated lung volumes, viral load in turbinates and lungs, viral shedding in upper respiratory tract, Macroscopic pathologic examination post mortem of lung weight, mean percentage of lesion affected lung tissue. Microscopic examination of inflammation parameters of nasal turbinates and lungs. Animal groups 3, 4 and 5 outperformed groups 1 and 2 in all macroscopic and in most microscopic parameters tested (data not shown).

Virus Replication in the Upper and Lower Respiratory Tract

On days 0, 1, 2, 3 and 4 after challenge, nose and throat swabs were taken from the animals under anesthesia. Four days after challenge, the ferrets were euthanized by exsanguination under anesthesia after which full-body grosspathology was performed and tissues were collected. Samples of the right nose turbinate and of all lobes of the right lung and the accessory lobe were collected and stored at −80° C. until further processing. Turbinate and lung samples were weighed and subsequently homogenized with a FastPrep-24 (MP Biomedicals, Eindhoven, The Netherlands) in Hank's balanced salt solution containing 0.5% lactalbumin, 10% glycerol, 200 U/ml penicillin, 200 μg/ml streptomycin, 100 U/ml polymyxin B sulfate, 250 μg/ml gentamycin, and 50 U/ml nystatin (ICN Pharmaceuticals, Zoetermeer, The Netherlands) and centrifuged briefly before dilution.

After collection, nose and throat swabs were stored at −80° C. in the same medium as used for the processing of the tissue samples. Quadruplicate 10-fold serial dilutions of lung and swab supernatants were used to determine the virus titers in confluent layers of MDCK cells as described previously (Rimmelzwaan G F et al., J Virol Methods 1998 September; 74(1)57-66).

Gross-Pathology and Histopathology

The animals were necropsied according to a standard protocol, as previously described (van den Brand J M et al., PLoS One 2012; 7(8)e42343). In short, the trachea was clamped off so that the lungs would not deflate upon opening the pleural cavity allowing for an accurate visual quantification of the areas of affected lung parenchyma. Samples for histological examination of the left lung were taken and stored in 10% neutral-buffered formalin (after slow infusion with formalin), embedded in paraffin, sectioned at 4 µm, and stained with haematoxylin and eosin (HE) for examination by light microscopy. Samples were taken in a standardized way, not guided by changes observed in the gross pathology. Semi-quantitative assessment of influenza virus-associated inflammation in the lung was performed as described previously (Table 4) (Munster V J et al., Science 2009 Jul. 24; 325(5939):481-3). All slides were examined without knowledge of the identity or treatment of the animals.

Virus Load in Lung and Upper Respiratory Tract Results

All ferrets of control groups 1 (i.n. saline) and 2 (parenteral TIV) showed high titers of replication competent virus in lung (mean titers; 5.7 and 5.5 log 10TCID50/gram tissue, respectively) and nasal turbinates (mean titers: 7.2 and 6.9 log 10TCID50/gram tissue, respectively) (Table 3). Ferrets of groups 3, 4 and 5 (i.n. Endocine™ adjuvanted split antigen pH1N1/09 vaccines) had no detectable infectious virus in their lungs and nasal turbinates. Ferrets of group 6 (i.n. Endocine™ adjuvanted whole virus at 15 µg HA) had no detectable infectious virus in their lungs and with a mean titer of 4.1 log 10TCID50/gram tissue a significant lower virus titer in the nasal turbinates as compared to control group 1 (p=0.02).

Intranasal immunization with Endocine™ adjuvanted pH1N1/09 vaccines reduced virus titers in swabs taken from the nose and throat as compared to saline or TIV administration. Virus loads expressed as area under the curve (AUC) in the time interval of 1-4 dpi, in nasal and throat swabs are shown in Table 3. Virus loads in nasal swabs of groups 3, 4 and 5 (i.n. Endocine™ adjuvanted split antigen at 5, 15 and 30 µg HA, respectively), but not of groups 2 and 6 were significant lower than in group 1 (group 1 versus groups 3-5; p≤0.03). Virus loads in throat swabs of group 1 and 2 were comparable and significant higher than in groups 3, 4, 5 and 6 (p≤0.03).

Gross-Pathology and Histopathology Results

Reduced virus replication in groups intranasally immunized with the Endocine™ adjuvanted pH1N1/09 vaccines corresponded with a reduction in gross-pathological changes of the lungs (Table 3).

The macroscopic post-mortem lung lesions consisted of focal or multifocal pulmonary consolidation, characterized by well delineated reddening of the parenchyma. All ferrets in control group 1 (i.n. saline) and group 2 (parenteral TIV) showed affected lung tissue with a mean percentage of 50% and 37%, respectively and corresponded with a mean relative lung weight (RLW) of 1.5 and 1.3, respectively (Table 3). In contrast, lungs in groups 3, 4, 5 and 6 (i.n. Endocine™ adjuvanted pH1N1/09 vaccines) were much less affected with mean percentages of affected lung tissue of 7-8%. The RLWs in these four Endocine™ vaccinated groups were in line with these observations (in a close range of 0.8 to 0.9).

The pulmonary consolidation corresponded with an acute broncho-interstitial pneumonia at microscopic examination. It was characterized by the presence of inflammatory cells (mostly macrophages and neutrophils) within the lumina and walls of alveoli, and swelling or loss of lining pneumocytes. In addition protein rich oedema fluid, fibrin strands and extravasated erythrocytes in alveolar spaces and type II pneumocyte hyperplasia were generally observed in the more severe cases of alveolitis. The histological parameters that were scored are summarized in Table 4. The most severe alveolar lesions were found in the control groups 1 (i.n. saline) and 2 (parenteral TIV). All parameters of alveolar lesions scored lowest in group 5, but in fact the differences between the groups 3, 4, 5 and 6 were not significant.

Conclusively, in lungs—The intratracheal challenge with H1N1 influenza A/Netherlands/602/2009 virus in this ferret model resulted in a slight to severe pneumonia. However, several animals, all from vaccinated groups, were not affected by macroscopically discernable lung lesions at all. Based on the macroscopic post-mortem evaluation of lung lesions (estimated % of lung affected), vaccinated (vaccine-A 15 µg HA) group 4 and vaccinated (vaccine-A 30 µg HA) group 5 equally suffered the least lung lesions with both a very low score of 7%, directly followed by vaccinated (vaccine-A 5 µg HA) group 3 and vaccinated (vaccine-B 15 µg HA) group 6 with both 8%. Placebo-PBS-treated group 1 animals suffered the most lung lesions with a marked mean score of 50%. Parenterally vaccinated control group 2 suffered slightly less but still prominent lung lesions with a mean 37%. The mean relative lung weights (RLW) were evidently in accordance with these estimated percentages of affected lung tissue, corroborating the validity of these estimated percentages of affected lung tissue.

The results of the microscopic examination of the lungs confirmed, for the majority of assessed parameters of lung lesions, the best scores for highest dosed vaccinated (vaccine-A 30 µg HA) group 5, and a gradual progression in respiratory lesions correlated to the decrease of HA dose of vaccine-A (groups 3 and 2, respectively). Vaccination with vaccine-B 15 µg HA practically equaled the results of lowest dose vaccine-A 5 µg HA (group 3). Placebo-PBS-treatment (group 1) scored by far the worst throughout all assessed histopathological parameters, closely followed by parenterally vaccinated control group 2. Remarkably, all intranasally vaccinated animals (groups 3, 4, 5, and 6) were protected from alveolar haemorrhage.

Overall conclusions—In conclusion therefore, based on the averaged pathology scores in this ferret virus challenge model, the vaccination with vaccine-A 30 µg HA (group 5) performed the best and resulted in the least respiratory laesions, whereas the placebo-PBS-treatment performed the worst and resulted in the most respiratory lesions. Vaccination with vaccine-A 15 µg HA (group 4) performed just slightly less compared to group 5, followed by vaccination with vaccine-A 5 µg HA (group 3) that performed practically similar compared to vaccination with vaccine-B 15 µg HA (group 6). All intranasally vaccinated animals, regardless of the dose and type of vaccine, were protected from alveolar haemorrhage. Parenteral control vaccination (group 2) performed poorly with marked respiratory lesions and just marginally better compared to the placebo-PBS-treatment (group 1).

Example 3

The Table 2 below and FIG. 4 compare the vaccine of the present invention with other products, FluMist and injectable vaccines in naïve ferrets.

TABLE 2

| Vaccine from | Ferrets (naïve) | Dose | Route | Vaccine strain (H1N1) | Evaluation strain (H1N1) | NT titer evaluation |
| --- | --- | --- | --- | --- | --- | --- |
| GSK* (GSK H1N1) | N = 6 | 15 ug HA, unadjuvanted | IM | A/California/7/09 | A/The Netherlands/602/09 | Before challenge (after 2 vacc) |

TABLE 2-continued

| Vaccine from | Ferrets (naïve) | Dose | Route | Vaccine strain (H1N1) | Evaluation strain (H1N1) | NT titer evaluation |
|---|---|---|---|---|---|---|
| GSK* | N = 6 | 15 ug HA, AS03$_A$ | IM | | | |
| Novartis # (Novartis TIV) | N = 3 | 15 ug HA, unadjuvanted | IM | A/Brisbane/59/07 | A/California/7/09 | Before challenge (after 2 vacc) |
| Medimmune # (pandemic LAIV) | N = 3 | 1 × 10$^7$ TCID$_{50}$ | IN | A/California/7/09 (ca) | | |
| GSK ¤ (GSK TIV) | N = 6 | 15 ug HA, unadjuvanted | SC | A/California/7/09 | A/The Netherlands/602/09 | Day 42 (after 2 vacc) |
| Eurocine Vaccines ¤ (Immunose ™ FLU) | N = 6 | 15 ug HA, Endocine 20 mg/ml | IN | | | |

*Baras et al. Vaccine 29 (2011) 2120-2126
Chen et al. JID 2011: 203
¤ Eurocine Vaccines: the present study GSK monovalent pandemic vaccine (GSK H1N1), Novartis trivalent inactivated vaccine (Novartis TIV), GSK trivalent inactivated vaccine (GSK TIV) groups had a neutralization titer (NT) titer below 15.

The results show that a vaccine composition of the present invention, Immunose™ FLU, here comprising 15 μg HA split influenza antigen with 20 mg/ml (2%) Endocine™ shows similar neutralizing titers to Medimmune's pandemic LAIV vaccine FluMist (see FIG. 5) and superior titers to injected vaccines whereas the non-adjuvanted TIV gives poor response.

ABBREVIATIONS USED IN EXAMPLES

HA Influenza virus hemagglutinin protein
TCID50 Tissue culture infectious dose 50%
PBMC Peripheral blood mononuclear cells
HI Influenza hemagglutination inhibition assay
SOP Standard Operation Procedure
PBS Phosphate buffered saline
EDTA Ethylene diamine tetraacetic acid
GMT Geometric mean titers (used to express serological data)
FCS Fetal Calf Serum (culture medium supplement)
VN Virus neutralization assay
DMSO Dimethyl Sulfoxide

The invention claimed is:

1. A method of immunizing a pediatric subject to reduce influenza virus shedding comprising:
   selecting a pediatric subject in need of a composition that reduces influenza virus shedding; and
   administering intranasally to said pediatric subject from newborn to 12 years of age a composition comprising:
   one or more non-live influenza virus antigen(s) selected from the group consisting of split virus, subunit influenza antigen, and recombinant antigens, and
   an adjuvant comprising mono-olein and oleic acid;
   wherein the mono-olein and oleic acid are in a 1:1 ratio, and wherein the combined concentration of the mono-olein and oleic acid is up to 3% (w/v).

2. The method of claim 1, wherein said pediatric subject is influenza naive.

3. The method of claim 1, wherein said pediatric subject is a child.

4. The method of claim 1, wherein the pediatric subject is a child that is less than 8 or 6 years of age.

5. The method of claim 1, wherein the pediatric subject is a child that is 2 months to less than 9 years of age, 6 months to less than 8 years of age, or 6 months to less than 7 years of age.

6. The method of claim 1, wherein the pediatric subject is an infant.

7. The method of claim 1, wherein the non-live influenza virus antigen is a split virus antigen.

8. The method of claim 1, wherein the adjuvant further comprises an aqueous medium.

9. The method of claim 1, wherein the composition comprises mono-olein in an amount within the range of: about 0.1 g to about 5.0 g, about 0.1 g to about 2.0 g, about 0.5 g to about 2.0 g, or about 0.5 g to about 1.5 g per 100 mL of the composition.

10. The method of claim 1, wherein the vaccine composition comprises oleic acid in an amount within the range of: about 0.1 g to about 5.0 g, about 0.1 g to about 2.0 g, about 0.5 g to about 2.0 g, or about 0.5 g to about 1.5 g per 100 mL of the composition.

11. The method of claim 1, wherein mono-olein together with oleic acid in an adjuvant mix is at the most: 3% w/v, 2% w/v or 1% w/v of the composition.

* * * * *